(12) United States Patent
Aojula et al.

(10) Patent No.: US 7,718,613 B2
(45) Date of Patent: May 18, 2010

(54) ARMED PEPTIDES

(76) Inventors: Harmesh Singh Aojula, Old Dutch Barn, Doctor Lane, Scouthead, Saddleworth, Oldham (GB) OL4 4AD; David John Clark, 6 Fields Drive, Sandbach, Cheshire (GB) CW11 1YB ( * ) Notice: Subject to any disclaimer, the term of this patent is extended or adjusted under 35 U.S.C. 154(b) by 1922 days.

(21) Appl. No.: 10/250,641

(22) PCT Filed: Jan. 4, 2002

(86) PCT No.: PCT/GB02/00033

§ 371 (c)(1), (2), (4) Date: Jul. 3, 2003

(87) PCT Pub. No.: WO02/059147

PCT Pub. Date: Aug. 1, 2002

(65) Prior Publication Data

US 2004/0063905 A1    Apr. 1, 2004

(30) Foreign Application Priority Data

Jan. 4, 2001    (GB) .................. 0100196.5

(51) Int. Cl.
*A61K 38/16*    (2006.01)
(52) U.S. Cl. ........................................ 514/12
(58) Field of Classification Search ....................... None
See application file for complete search history.

(56) References Cited

FOREIGN PATENT DOCUMENTS

| WO | WO 9841535 A2 | * | 9/1998 |
| WO | WO 9920252 A1 | * | 4/1999 |
| WO | WO 9938009 A1 | * | 7/1999 |

* cited by examiner

*Primary Examiner*—Andrew D Kosar
(74) *Attorney, Agent, or Firm*—Dunlap Codding, P.C.

(57) ABSTRACT

This invention relates to peptides useful for releasing active agent in the fields of diagnostics and drug delivery.

7 Claims, 14 Drawing Sheets

SEQUENCE LISTING

```
<160> NUMBER OF SEQ ID NOS: 13

<210> SEQ ID NO 1
<211> LENGTH: 29
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (16)..(16)
<223> OTHER INFORMATION: biotinylated

<400> SEQUENCE: 1

Glu Ala Ala Leu Ala Glu Ala Leu Ala Glu Ala Leu Ala Glu Gly Lys
1               5                   10                  15

Pro Ala Leu Ile Ser Trp Ile Arg Arg Arg Leu Gln Gln
            20                  25

<210> SEQ ID NO 2
<211> LENGTH: 29
<212> TYPE: PRT
<213> ORGANISM: Artificial Sequence
<220> FEATURE:
```

```
<223> OTHER INFORMATION: synthetic peptide
<220> FEATURE:
<221> NAME/KEY: MISC_FEATURE
<222> LOCATION: (1)..(1)
<223> OTHER INFORMATION: Myristoylated

<400> SEQUENCE: 2

Glu Ala Ala Leu Ala Glu Ala Leu Ala Glu Ala Leu Ala Glu Gly Lys
1               5                   10                  15

Pro Ala Leu Ile Ser Trp Ile Arg Arg Arg Leu Gln Gln
            20                  25

<210> SEQ ID NO 3
<211> LENGTH: 29
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (27)..(27)
<223> OTHER INFORMATION: Myristoylated

<400> SEQUENCE: 3

Glu Ala Ala Leu Ala Glu Ala Leu Ala Glu Ala Leu Ala Glu Gly Lys
1               5                   10                  15

Pro Ala Leu Ile Ser Trp Ile Arg Arg Arg Lys Gln Gln
            20                  25

<210> SEQ ID NO 4
<211> LENGTH: 29
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (29)..(29)
<223> OTHER INFORMATION: Myristoylated

<400> SEQUENCE: 4

Glu Ala Ala Leu Ala Glu Ala Leu Ala Glu Ala Leu Ala Glu Gly Lys
1               5                   10                  15

Pro Ala Leu Ile Ser Trp Ile Arg Arg Arg Gln Gln Lys
            20                  25

<210> SEQ ID NO 5
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Myristoylated

<400> SEQUENCE: 5

Glu Ala Ala Leu Ala Glu Ala Leu Ala Glu Ala Leu Ala Glu Gly Lys
1               5                   10                  15
```

Pro Ala Leu Ile Ser Trp Ile Arg Arg Leu Gln Gln
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (16)..(16)
<223> OTHER INFORMATION: Branched off sequence from Lysyl residue:
      ELFTNR

<400> SEQUENCE: 6

Glu Ala Ala Leu Ala Glu Ala Leu Ala Glu Ala Leu Ala Glu Gly Lys
1               5                   10                  15

Pro Ala Leu Ile Ser Trp Ile Arg Arg Arg Leu Gln Gln
            20                  25

<210> SEQ ID NO 7
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (13)..(13)
<223> OTHER INFORMATION: Branched off sequence from Lysyl residue:
      TLLEFLLEELLEFL

<400> SEQUENCE: 7

Gly Ile Gly Ala Val Leu Arg Val Leu Thr Thr Gly Lys Pro Ala Leu
1               5                   10                  15

Ile Ser Trp Ile Arg Arg Arg Arg Gln Gln
            20                  25

<210> SEQ ID NO 8
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (29)..(29)
<223> OTHER INFORMATION: Myristoylated

<400> SEQUENCE: 8

Glu Ala Ala Leu Ala Glu Ala Leu Ala Glu Ala Leu Ala Glu Gly Lys
1               5                   10                  15

Pro Ala Leu Ile Ser Trp Ile Arg Arg Arg Gln Gln Lys
            20                  25

<210> SEQ ID NO 9

```
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Myristoylated

<400> SEQUENCE: 9

Trp Glu Ala Ala Leu Ala Glu Ala Leu Ala Glu Ala Leu Ala Glu His
1               5                   10                  15

Leu Ala Arg Ala Leu Ala Glu Ala Leu Glu Ala Leu Ala Ala
            20                  25                  30

<210> SEQ ID NO 10
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Myristoylated

<400> SEQUENCE: 10

Trp Glu Ala Leu Ala Glu Ala Leu Ala Glu Ala Leu Ala Glu His Leu
1               5                   10                  15

Ala Lys Ala Leu Ala Glu Ala Leu Glu Ala Leu Ala Ala
            20                  25

<210> SEQ ID NO 11
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (13)..(13)
<223> OTHER INFORMATION: Branched off sequence from Lysyl residue:
      TLLEFLLEELLEEL

<400> SEQUENCE: 11

Gly Ile Gly Ala Val Leu Arg Val Leu Thr Thr Gly Lys Pro Ala Leu
1               5                   10                  15

Ile Ser Trp Ile Arg Arg Arg Arg Gln Gln
            20                  25

<210> SEQ ID NO 12
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (13)..(13)
<223> OTHER INFORMATION: Phosphorylated
```

```
-continued

<400> SEQUENCE: 12

Trp Glu Ala Ala Leu Ala Glu Ala Leu Ala Glu Ala Ser Ala Glu His
1               5                   10                  15

Leu Ala Arg Ala Leu Ala Glu Ala Leu Glu Ala Leu Ala Ala
            20                  25                  30

<210> SEQ ID NO 13
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Myristoylated

<400> SEQUENCE: 13

Leu Glu Ala Ala Leu Ala Glu Ala Leu Glu Ala Leu Ala Ala Gly Lys
1               5                   10                  15

Pro Ala Leu Ile Ser Trp Ile Arg Arg Arg Arg Gln Gln
            20                  25
```

ARMED PEPTIDES

FIELD TO WHICH THE INVENTION RELATES

This invention relates to the fields of drug delivery and diagnostics. In particular the invention relates to the release of active agents from peptides or from liposomes containing such peptides or cells containing such peptides in drug delivery or diagnostic applications.

BACKGROUND

Cytolytic peptides or cytolysins have previously been used to release active agents or "payload" from liposomes or cells. The mode of action for such peptides involves perturbation of the liposome or cellular membrane. These peptides include toxins from insects, fish, antibiotic peptides and synthetic peptides such as melittin, alamethicin, gramicidin, magainin and pardaxin, GALA, KALA, hemagglutinin subunit HA-2. Natural potent cytolytic peptides are found widely from insects to mammals, particularly as antimicrobial peptides or defensins, where they are involved in innate defence at mucosal membranes and as cytolysins in lymphocytes. In order to target and localise the cytolytic action of such peptides, a number of specific steps e.g. activating synthesis, release from lysosomes, cleavage of pro-peptides is required. The biological delivery activity of such peptides is tightly controlled at the cellular and molecular levels. Biologically, cytolysin activity is cloaked by sophisticated mechanisms available within and between cells butthese mechanisms are diagnostically and therapeutically less exploitable. This has therefore hindered the use of cytolysins in diagnostic and therapeutic applications.

Whilst much sought after, there are remarkably few simple and rapid homogeneous biodetection methods.

Owing to their inferior sensitivity and non specific variable background, compared to the automated heterogeneous technology which is now widespread in immunodiagnostics and high throughput screening, it has not always been possible to develop homogeneous assays for different analytes. Liposomes have, previously, been utilised in homogenous assays using complement-mediated lysis (Anal. Biochem. 118 (1981) 286-293.) However, such assays are considered unreliable as they involve many labile components, any one of which may become inactivated eliminating payload release. The development of a homogenous liposomal assay using non-specifically labelled digoxin melittin as the lytic agent was reported as an alternative to the complement assay (J.Immunol. Methods. 70 (1984)133-140). This method, however, has not gained widespread use as the preservation and stability of lytic activity, as well as solubility of the conjugates posed problems largely restricting the use of this cytolytic peptide to measure digoxin. This may be expected, primarily due to the uncertainties involved in the production of useful cytolysin conjugates by relying solely on natural peptides with multiple labelling sites, most of which are critical for peptide function and, thus, not ideally placed for retaining high activity if modified. Furthermore, the degree of modulation in activity of these conjugates is often inadequate resulting in high background signals. Owing to these difficulties when using natural peptides, others have used conjugates with a larger cytolysin, namely phospholipase C, non-specifically labelled with analytes (J.Immunol. Methods 170 (1994) 225-231). Such conjugates had superior solubility and greater retention of activity after modification. However, only 75 to 85% activity was specifically inhibited in the presence of anti-serum, which is comparable to the level of inhibition normally used for measuring digoxin with melittin-oubain conjugates. A reliable assay should only permit the release of marker molecules upon external trigger and the background leakage should approach zero or at least remain constant over the assay period. To our knowledge neither of these conditions have been satisfactorily addressed by homogeneous liposomal assays, without changing to a heterogeneous assay configuration. Consequently, with such assays there is always a danger of the background signal progressively interfering with the analyte dependent signal. Some of the long term background problems arising from the use of liposome reagents per se can be overcome by the use time resolved fluorimetry, in which a larger molecular weight protein chelator conjugate is encapsulated in the liposomes, allowing fluorescent detection upon cytolysin mediated complexing with ions such as $Eu^{3+}$(Anal. Biochem 238 (1996) 208-211). Even with these assays, the inherent problems of the non-specific lysis by uninhibited conjugates as well as optimising conjugates to produce adequate activity, remain. Consequently, such assays need to be performed under well-controlled laboratory conditions and at fixed times against the varying background signal.

Liposomes have been used more widely in drug delivery rather than in diagnostic applications and or as imaging agents, however, in all cases there has been little progress made with the use of liposomes, efforts being mainly devoted to developing different lipid formulations to try to achieve controlled and quantitative release of active agent or payload in response to a trigger.

For a reliable assay, the release of detectable marker molecules should only occur in response to an external trigger and any leakage of marker molecules should be minimal for example, approaching zero, or at least remain constant over the assay period. Consequently, in such assays there is always a danger of background signal or interference caused by the progressive release of marker molecules.

Our earlier patent application WO98/41535 (PCT/GB98/00799) describes peptides which can be efficiently cloaked and used to release a "payload" in a controlled manner. The peptides disclosed in that application were non-responsive to pH change particularly over a narrow range between pH 6.5 and 7.4. On the contrary, in most cases, lowering of the pH would result in the lowering of peptide activity. A number of pH sensitive peptides have been used to release payload from liposomes under acidic conditions (*Advanced Drug Delivery Reviews* 38 (1999) 279-289). For these peptides the triggering range is, however, far from physiological pH, usually requiring pH values lower than 6 to release payload from liposomes.

GALA is one of the most efficient pH specific peptide. For this peptide Calcein release from liposomes has been demonstrated at values lower than 6. There are many other pH specific peptides, such as Influenza virus HA-2 N-terminal peptide, EALA, JTS1 and Rhinovirus VP-1 N-terminal peptide which have been shown to release liposome contents in low pH environments such as the endosome where the pH is reported to be well below 6 and typically 5. There are several pH sensitive peptides known in the literature to destabilize liposome membranes. However they are usually triggered at very low pH (5.5) and consequently have found little or no use in drug delivery, for example, to tissues or tumours where the pH difference between normal and diseased areas can be less than a one pH unit. Their major use thus remains endosome delivery.

The strategy of micro-environmental pH change in tissues to induce preferential release of drugs from liposomes requires peptides to respond over a narrow pH change, closer to the physiological range. To our knowledge there are no reported peptides which trigger release of payload from liposomes efficiently and close to physiological pH levels of 7.4 while their background biological activity remains low or zero at or close to pH 7.4.

A peptide named "helical erythrocyte lysing peptide" (HELP) (Protein Eng. (1992), 5, 321) is known to lyse red blood cells and has been shown to trigger release of haemoglobin below pH 6.5 only. This peptide is, however, specific to lysing cells and there are no reports showing lysing of liposomes. We have shown that liposomes could not be lysed in a pH specific manner using this peptide.

WO97/38010 relates to fusogenic liposomes and delivery systems for transporting-materials such as drugs, nucleic acids and proteins. These systems work by fusion of liposomes and at pH values lower than 6.

DESCRIPTION OF THE INVENTION

According to one aspect of the invention there is provided a cytolytic or agent delivery peptide, wherein the cytolytic or agent delivery activity of the peptide is modulated by changes in one or more parameters which directly or indirectly affect the peptide, wherein changes in one or more such parameters leads to cytolysis or agent delivery by the peptide at a pH close to physiological values. The invention therefore provides a "cloakable" cytolytic or agent delivery peptide whose activity can be harnessed and maintained low by arming but triggering only with another parameter or stimuli. The invention finds uses in in vitro, in vivo diagnostics, and in the delivery and targeting of drugs. Preferably, the cytolytic or agent delivery activity is modulated by changes in more than one parameter. More preferably, one such parameter is pH.

According to another aspect of the invention there is provided a cytolytic or agent delivery peptide, where the cytolytic or agent delivery activity is modulated by a change in pH, from a starting pH to a modulating pH where the starting pH is close to physiological pH values. Preferably the pH value is less than 7.40. Thus in certain disease conditions in which a change of pH occurs as cells go from a non-diseased to a diseased state, an active agent can be released by the peptides in response to that pH change.

The parameter may be for example pH, the effect of a ligand e.g for a receptor or enzyme, temperature, light, ultrasound; redox potential, DNA, nucleic acid binding, or binding of the peptide to liposome, to form a non-leaky complex i.e. one where the active agent or payload is not released by the liposome until deliberately triggered. pH is a preferred parameter.

The peptides are designed to increase in hydrophobicity as the pH decreases from neutral to slightly acidic while retaining substantial positive charge. The prior art pH sensitive peptides (Parente et al, Biochem, (1990) 29, 8720); Subbarae et al, Biochem (1987) 26, 2964-2972) have predominantly Glu residues ($pK_a$ about 5) and cannot fulfill the required pH sensitivity for triggering closer to neutral. We find that the negative character can be counterbalanced by carefully including basic residues into the sequence resulting in desired pH sensitivity. Similarly the hydrophobic character can be counterbalanced by including fatty acid or modifications containing alkyl chains carefully positioned in the sequence. Suitable modifications include myristoyl, palmitoyl, dioleoyl, phospholipid, farnesyl, undecyl, octyl and geranyl. The hydrophobic-anionic-cationic character of a peptide is a crucial factor in achieving a narrow triggering range on setting closer to neutral but off setting at physiological pH. The triggering range can be tuned to within the 6.5 to 7.4 pH range.

Examples of the peptides of the invention are given in Table 1. Many of the peptides in our table 1 could be modified to produce multi-triggering properties. For instance peptide 13 in particular could be phosphorylated on Ser to bring about inactivation (like peptide 12) and it could be biotinylated on Lys to inactivate with avidin binding (as in peptide 1) and it could in addition be inactivated by DNA binding on C terminal. Thus if desired its pH triggering properties do not need to be utilised.

In one embodiment, the invention provides a pH sensitive cytolytic peptide, having a cloaking site, and which is integrated with or can integrate with a lipid vesicle and can be activated closer to physiological pH in order that antibody or receptor binding at the cloaking site is near optimum while its activity at physiological pH can be harnessed and maintained low by control of pH levels affecting the peptide. In a preferred embodiment the integration with liposomes is achieved by covalently linking a hydrophobic group such as a fatty acid onto the peptide. There are several other lipids such as palmitic acid or isoprenyl groups which could also be used to conjugate liposomes with peptides. Further ways of peptide incorporation include: covalent linkage to phospholipid, binding to receptors or ligands pre-incorporated on liposome surface or cells, encapsulation of the peptide in the liposomes, attachment of hydrophobic or amphiphilic segments to peptides and electrostatic binding to charged membranes.

The dual switch feature embodied in peptides of the invention has potential uses in drug delivery systems.

For example, in the case of a pH-responsive cytolytic or agent delivery peptide, the peptide could be maintained in an inactivated form by a proteolytic sensitive sequence, the peptide would then be activated after proteolytic cleavage and when the pH conditions are met (usually acidic).

For instance the cloaking site can be phosphorylated and triggering would then involve dephosphorylation and pH change. Alternatively, the cloaking site may be modified with a proteolytic sensitive sequence, cleavage of this sequence then activating the peptide.

In the case of a pH-responsive peptide, the peptide could be inactivated by DNA binding, the peptide would then be activated after DNA dissociation and when the pH conditions are right (usually acidic).

A pH-responsive peptide could initially be inactivated by antibody binding and then activated in presence of an analyte or an epitope and when the pH conditions are right (usually acidic).

A pH-responsive peptide-liposome complex could be targeted by the inclusion of a cell-specific sequence to particular cells in an inactivated state and adapted so that the microenvironment of the cells activates the peptide to release payload.

A pH sensitive peptide could include a specific sequence so that it can be targeted to cells in an inactivated state, triggering then being effected with external stimuli or by addition of pH modulator. Examples of pH modulation include glucose-mediated decreases of pH in some malignant tissues and bolus injection of MIBG (meta-iodobenzylamine) with glucose resulting in pH activation to release payload from the peptide. There are many examples of cell targeting sequences. Endothelial cells in angiogenic vessels within the tumour have markers such as alpha integrins. The motif Arg-Gly-Asp (RGD) present in peptide structures binds selectively to integrins. Similarly there are several other motifs such as NGR, GSL. The screening of phage display peptide libraries is greatly enhancing discovery of new targeting sequences. For instance, several prostate-specific antigen (PSA) binding peptides are known.

The peptide may have continuous stretches of basic and acidic sequences and trigger close to physiological pH to effect lysis of biomembranes or condense/decondense DNA closer to physiological range. Preferably a pH sensitive peptide comprises a highly basic sequence at one end and a highly acidic sequence at another end and the overall Pi value lies between 6.4 and 9.

In peptides in accordance with the invention, changes in one or more parameters leads to cytolysis or agent delivery by the peptide at a pH close to physiological values.

In particular, the pH value at which the cytolytic or agent delivery activity occurs may be less than 7.40, preferably between pH 6.5 and 7.4; pH 6.6 and 7.4; pH 6.7 and 7.4; pH 6.8 and 7.4; pH 6.9 and 7.4; pH 7.0 and 7.4; pH 7.1 and 7.4; or pH 7.2. and 7.4.

The hydrophobicity of the peptide may increase as pH decreases whilst retaining a substantial positive charge.

The cytolytic activity or agent delivery activity may include releasing an agent which has been bound to the peptide.

The peptide may have a predominantly negatively charged portion with a relatively low Pi value and a predominantly positively charged portion with a relatively high Pi value. The negatively charged portion may contain at least two amino acids having a relatively low Pi value. The said at least two amino acids may be selected from glutamine acid and aspartic acid.

Preferably the Pi value of the negatively charged portion is about 4.

The positively charged portion contains at least two amino acids with a relatively high Pi value. The Pi value of the positively charged portion may be about 9. The said at least two amino acids may be selected from lysine, arginine or histidine.

The positively charged or negatively charged portions may be at or near the ends of the peptide or provided by side chains of the peptide.

The negatively charged portion may have the composition:

$$X_{n1}Y_{n2}$$

where n1 is ≧2; and n2 is 7−n1 and where X=glutamic acid and/or aspartic acid

Y is any amino acid other than lysine, arginine or histidine.
The positively charged portion may have the composition:

$$A_{n1}B_{n2}$$

where n1≧2; and n2=Z−n1 and where X is glutamic acid and/or aspartic acid

B is any amino acid other than glutamic acid or aspartic acid
Z=any integer from 7 to 14.
Preferably Z=9, or 7. Most preferably Z=9.

Other aspects of the invention are apparent from the appended claims.

A peptide can be used to form complexes with liposomes without payload. The complex can then be used to load agents or "payload" into liposomes at an acidic pH the payload then being trapped by raising the pH.

An armed peptide can be encapsulated into liposomes whereby lysis of the liposomes takes place from within the liposomes by unarming the trigger. The trigger can be unarmed by, for instance, proton movement, in case of a pH-responsive peptide, which can be aided or unaided by protonophores or by cofactors, in case of an enzyme sensitive sequence or by other activation means.

According to another aspect of the invention there is provided a method of releasing an active agent from a lipid vesicle the method comprising altering more than one parameter relating to a cytolytic peptide whereby the cytolytic peptide is activated to cytolyse the lipid vesicle containing the active agent.

The lipid vesicle may be for example a cell or a liposome.

By using more than one trigger to cloak cytolytic peptides in diagnostic methods according to the present invention, the background signal can be improved and maintained low and stable allowing simpler assay configurations and more predictable development for multiple of analytes. This invention provides peptide-liposome complexes which trigger close to physiological conditions. The complexes can respond to slight variations in physiological pH. Further aspects of the invention relate to controlling triggering of peptides or their liposome complexes which can be effected by altering at least two or more parameters one of which is used to arm the release of payload as a "safety catch". In the preferred embodiment the peptides are integrated with liposomes as complexes.

Definitions

The following definitions are given by way of explanation:

The term "peptide" used in this specification embraces polypeptides and proteins formed from natural, modified natural and synthetic amino acids.

The term "cytolysis" means the disruption of particles such as cells, liposomes, biomembranes or polymers.

The term "active agent" includes non-biologically active substances such as imaging agents or fluorophores.

The term "payload" means anything encapsulated in a liposome and which can be released by the peptides of the invention.

BRIEF DESCRIPTION OF THE DRAWINGS

Peptides, peptide/liposome complexes, methods of drug delivery, diagnosis in accordance with the invention will now be described, by way of example only, with reference to the accompanying drawings, FIGS. 1 to 15, in which:

FIG. 1 is a schematic illustration of the concept of arming peptide-liposome complexes in accordance with the invention;

FIGS. 2A and 2B are graphs illustrating the detection of biotin by pH arming peptide 1 (table 1);

FIGS. 3A, 3B and 3C are graphs and 3D is a photograph illustrating an experimental biotin assay with peptide 1 from table 1;

FIG. 4 is a graph showing the effects of different pH levels in the release of dye from liposomes with various peptides from table 1.

FIG. 5 is a graph and shows the results of experiments involving both antibody binding and pH arming at pH 7.4.

FIG. 6 is a graph illustrating the results of experiments with an assay for the detection of VTB epitope;

FIG. 7 is a graph illustrating the results of experiments with an assay for the detection of VTB subunit;

FIG. 8A to F are graphs illustrating the release of dye from peptide liposome complexes at different pH levels;

FIG. 9 is a graph showing the results of testing the complex of peptide 1 tested 40 minutes from preparation;

FIG. 10 is an image of a Rif tumour after administration of liposomes and pH armed peptide liposome complex; and FIG. 11 is a graph showing the release of dye from liposomes in a tumour;

FIG. 12 is a graph showing the release of dye from liposomes in a tumour;

Competitive reactions could be used, particularly when the affinity or immuno-specific trigger is armed by another mechanism (e.g., pH), which could also be expected to improve the practical fidelity of a displacement trigger. A pH sensitive peptide of sequence Myr-EAALAEALAEALAEGK*PALISWIRRRLQQ-anide was designed, modified with biotin at cloaking site (*) and integrated with liposome.

This peptide-liposome complex exhibits pH dependent activity depending on concentration of peptide used. The modified peptide retained its activity and pH responsive properties upon modification with biotin. At acidic pH the peptide-liposome complex is active while at alkaline pH the complex remains inactive (FIG. 2). In FIG. 2, the curves from top to bottom represent (i) Peptide at pH 6.6, (ii) Peptide at pH 8 and (iii) background signal in the absence of any peptide. In FIG. 2A, the curves from top to bottom represent peptide in the presence of (i) 11 piccolos of biotin and 1,2 fold excess avidin at pH 6.6, (ii) 1.2 fold excess avidin at pH 6.6, (iii) 11 piccolos of biotin and 1.2 fold avidin at pH 8 and (iv) 1.2 fold excess avidin at pH 8. Further the complex could be efficiently cloaked with avidin binding. Data in FIG. 2 reveals that in the presence of analyte (biotin) detection could be triggered only at acidic pH while only slight release was noted at pH 8 thus providing evidence for dual switched peptide where both the affinity reaction and pH are required to release liposome contents.

The biotin assay using pH sensitive peptide was repeated in a glass vial which could be illuminated with a small torch or blue LED light source. Specifically, the vials contained 1.2 ml of biotinylated hybrid peptide (17 nM) in PBS buffer pH 6.2 containing calcein liposomes (4 mM lipid) and 1.2 fold excess avidin. Biotin was present in vials 3 to 6 in increasing concentration. Vials are as follows: (1) Background sample containing liposomes only, (2) no biotin, (3) 12 pmoles biotin, (4) 15 pmoles biotin, (5) 17 pmoles biotin, (6) 50 pmoles Samples were illuminated by simple 3 mm blue diodes from underneath the cuvettes. Photographs in the order top to bottom, were taken at indicated times from addition of liposomes. The actual fluorescence readings taken on a fluorimeter at five minute period are also shown graphically. Five minutes after the addition of all reagents the fluorescence became clearly visible to the naked eye compared to the background which remained low and constant allowing detection of 12 picomole of biotin rapidly without any instrumentation. (FIG. 3). However, instrumentation available in most laboratories (e.g., fluorescence, absorption, luminescence, electrochemical, biosensors), can also be used for quantitative analysis by changing the signal development molecules incorporated into the liposomes.

The general concept of using eloaked cytolytic peptides with bio specifically switched activity is illustrated schematically in FIG. 1. Structural and covalent modifications at the cloaking site prevents action of the peptides on biomembranes by one or more mechanisms (FIG. 1). These may include pH, ligand, steric hindrance, (e.g., antibodies, avidin) and redox titration of ionisable moieties. When this is reversed by back titration of the ionisable groups, by release of the bound protein or by enzymatic cleavage of the cloaking moiety, biomembranes can be permeabilised to small and large molecules. This can be used for the controlled release of diagnostic or therapeutic payloads from liposomes or may be applied directly to permeabilise cells. The use of more than one trigger to activate the peptides would be expected to improve the fidelity or specificity of the process, and, in principle, any combination could be used. For example, the use of a physiologically-relevant physicochemical activation (e.g., pH, redox) combined with an immunospecific trigger may be used to control cytolysin action on cells, to release amplifiers from liposomes for sensitive diagnostic tests on specific viable micro-organisms and for the bioresponsive release of drugs from liposomes.

Integration of peptide assemblies into lipid bilayer can be driven by introducing non charged terminal to form tethering site while cloaking site is regio-specifically located at position near the central part of peptide most likely to affect its function quantitatively by binding reactions. Line is drawn to show the polar-apolar interface. Mechanisms involved in activating peptides could include steric, pH, redox, enzymic cleavage or a combination for multi-triggering with the result that dissociation of the cloaking molecule and presence of trigger frees the cytolytic peptide to breach the membrane. In the schematic above peptide is allowed to form complex with liposomes (lipid bilayer shown) while cloaked with receptor. The uncloaked peptide although liposome associated remains inactive until another parameter such as pH is altered and peptide becomes active to cause lysis. It is obvious to state that cloaking can be done either before or after liposome complex is formed to function in competitive or displacement modes.

EXAMPLES

The primary sequence of the peptides are given in table 1. The cytolytic peptides were manually synthesised by solid phase t-Boc chemistry using 0.5 mmol of p-methylbenzhdrylamine (MBHA) resin. Side chain protections for amino acids (BACHEM UK) were 2-chlorobenzyloxycarbonyl for Lysine; p-toluenesulfonyl for Arg, Benzyl for threonine, serine and glutamic acid. Couplings were made using 1.5 mM amino acid, 1.5 mMoles benzotriazol-1-yl-oxytris (dimethylamino) phosphonium hexafluorophosphate (BOP) and 4.5 mM N,N-diisopropylethylamine (DIPEA) in N,N-dimethylformamide (DMF) for 40 mins. Second coupling was used when necessary to drive the reaction to almost completion (>99.8%). Myristic acid was coupled in same manner as an amino acid. In the case of peptides where the sequence was branched off from Lysyl residue (sequences shown in brackets in table 1) we used Fmoc protection on the ϵ-amino which was selectively deprotected using 20% piperidine and synthesis continued as usual. At the end of synthesis the peptide was cleaved using HF in the presence of 0.5 g p-thiocresol and 0.75 g p-cresol as scavengers. The peptides were purified on a C-4 reverse phase semi-preparative column (Vydac C-4, 250×4.6 mm) using an acetonitrile/0.1% TFA gradient. The HPLC purity of the peptides was determined by analytical reverse phase HPLC. No peptides were used below 95% purity level. Characterisation was made using MALDI (Thermobioanalysis) mass spectrometry.

Table 1 peptideshows examples of peptides which were synthesised and which were shown to trigger in slightly acidic buffers whilst exhibiting very low or no activity at pH 7.4.

TABLE 1

Chemically modified peptides

| SEQ ID NO: | Sequence |
|---|---|
| 1. | Myr-EAALAEALAEALAEGK(biotinyl)PALISWIRRRLQQ-amide |
| 2. | Myr-EAALAEALAEALAEGKPALISWIRRRLQQ-amide |
| 3. | Myr-EAALAEALAEALAEGKPALISWIRRRK(myristoyl)QQ-amide |
| 4. | Myr-EAALAEALAEALAEGKPALISWIIQQK(myristoyl)-amide |
| 5. | Myr-EAALAEALAEALAEGKPALISWIRRLQQ-amid |
| 6. | Myr-EAALAEALAEALAEGK(ELFTNR)PALISWRRRLQQ-amide |
| 7. | Myr-GIGAVLRVLTTG(TLLEFLLEELLEFL)KPALISWIRRRQQ-Amide |
| 8. | Myr-EAALAEALAEALAEGKPALISWIRRRQQ K(Myr)-Amide |
| 9. | Myr-WEAALAEALAEALAEHLARALAEALEALAA-Amide |
| 10. | Myr-WBALAEALAEALAEHLAKALAEALEALAA-Amide |
| 11. | Myr-GIGAYLRVLTTG(TLLEFLLEELLEEL)KPALISWIRRRRQQ-Amide |
| 12. | Myr-WEA ALA EAL AEA S(Phospho)AE HLA RAL AEA LEA LAA-Amide |
| 13. | Myr-LEAALAEALEALAAGKPALISWIRRRRQQ-Amide |

For preparing biotinylated peptides the peptide (0.02 mmole) was dissolved in 4 ml DMF and Biotin N-hydroxysuccinimide (0.1 mmole) added followed by DIPEA (0.3 mmole) and the mixture stirred. In all these preparations the reaction was allowed to proceed until completion as judged by the decline in amine content using a ninhydrin assay. The solvent from reaction mixtures was removed under vacuum and the product was purified by reverse phase HPLC on a C-4 preparative column using acetonitrile and 0.1% TFA gradients. Characterisation was made by mass spectrometry as above.

Liposomes with Payload

Liposomes encapsulating calcein dye were prepared by an extrusion method (Biochim. Biophys. Acta, 812 (1985) 55). Phophatidylcholine (50 mg) and cholesterol (13.08 mg) which had been dissolved in 4 ml of 50% v/v chloroform methanol solution were evaporated to form a lipid film in a round bottom flask. If it is essential to follow the fate of liposomes a lipohilic-dye such as DiI (50 µg) could be incorporated into the lipid film prior to hydration. The film was then hydrated with 4 ml of 120 mM calcein solution prepared in 10 mM sodium phosphate 20 mM Sodium chloride buffer pH 7.4. Liposomes were formed by 10 extrusion cycles through 0.2 micron or 0.1 um polycarbonate filters using the Liposofast 100 (Avestin) extruder device. The non encapsulated dye was removed by gel filtration on a PD-10 column using iso-osmotic buffer. The total lipid concentration of the liposomes was measured by the Stewart assay and adjusted to 3 mg per ml.

Closer to Physiological pH Switching Properties

Figure 4:
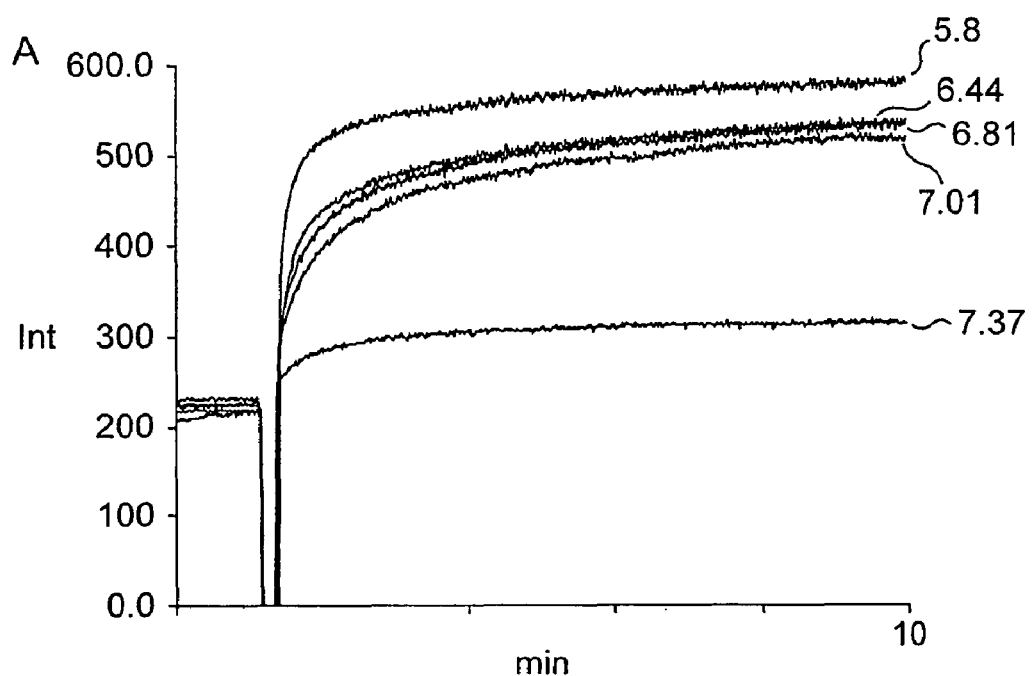
Figure 4:
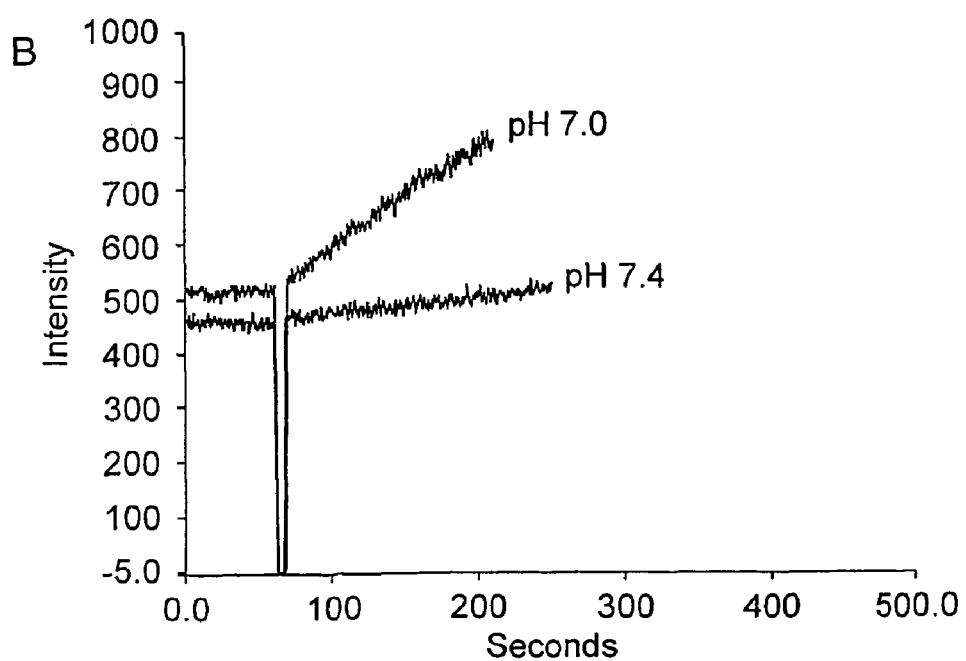
Figure 4:
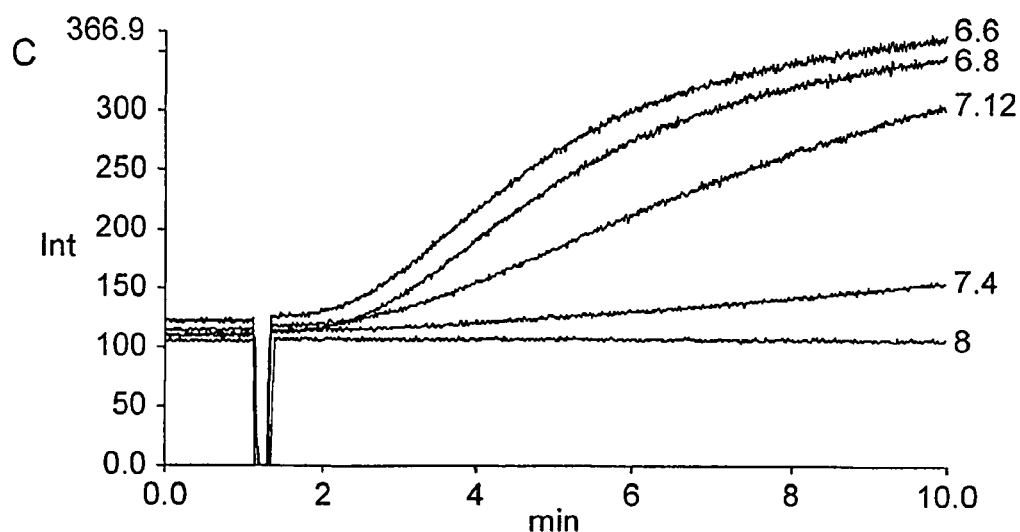

The cytolytic activity of pH-responsive peptides was followed by adding 2 or 3 µl of liposomes to a 2 ml assay volume and continually recording fluorescence. Buffers were made of 10 mM Na phosphate, 140 mM NaCl, 1 mM EDTA, 5 mM HEPES at several different pH values. The pH profiles of the various peptides from table 1 peptideshowing triggering around pH 7 are shown in FIG. 4. Specifically, FIG. 4 shows the results of peptides 2, 7 and 9 acting on liposomes. In the experiments 2 ml of 10 mM Na phosphate, 140 mM NaCl, 1 mM EDTA, 5 mM HEPES buffer (at pH values indicated on the figure) containing liposomes (4 µM lipid) and (A) 14 nM peptide 2, (B) 20 nM peptide 7 (C) 45 nM peptide 9. In all cases peptides were added indicated by sharp dip in fluorescence were used. The pH values are as indicated for each trace. Note that this pH is close to optimum for most receptors and such triggering has never been demonstrated before. In general, it is well documented that many proteins including receptors, enzymes and antibodies has pH optimum usually closer to physiological value. On either side of the pH optimum the binding activity is reduced. However in general as activity profile is typically bell shape most proteins would tolerate at least a pH unit shift from optimum. Obviously the closer the results are to pH 7.4 the higher chances their are for efficient binding with target proteins or receptors.

Detection of Biotin by pH Arming

Figure 1:
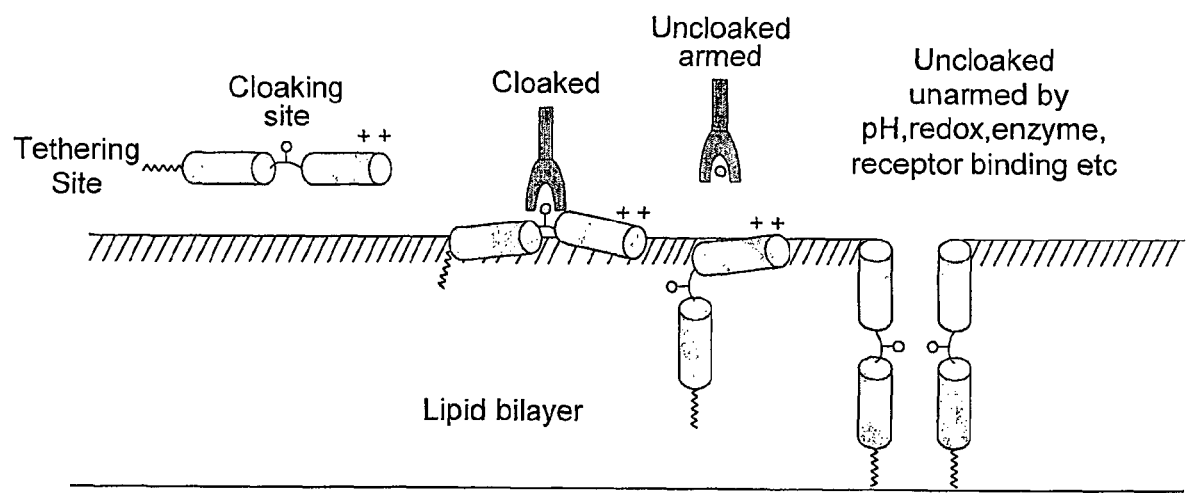
Figure 2:
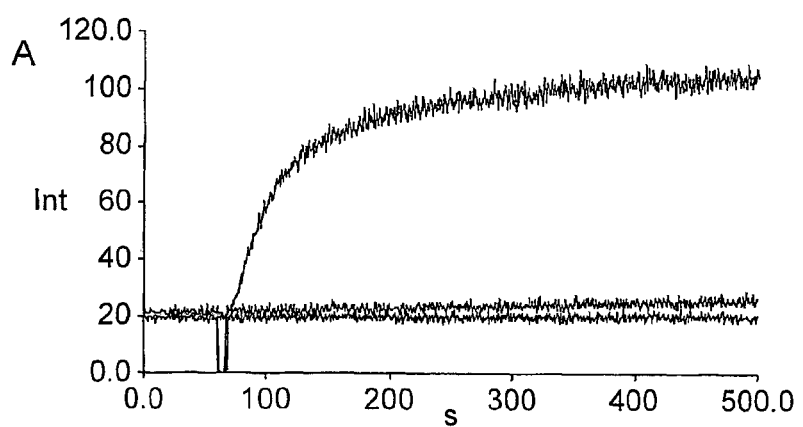
Figure 2:
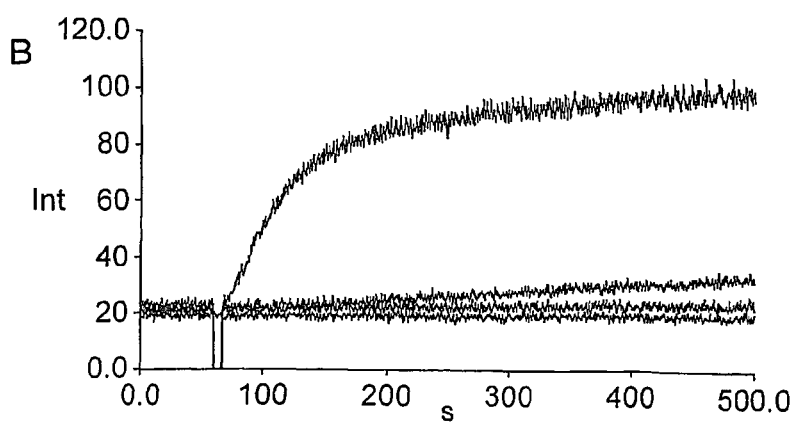
Figure 3:
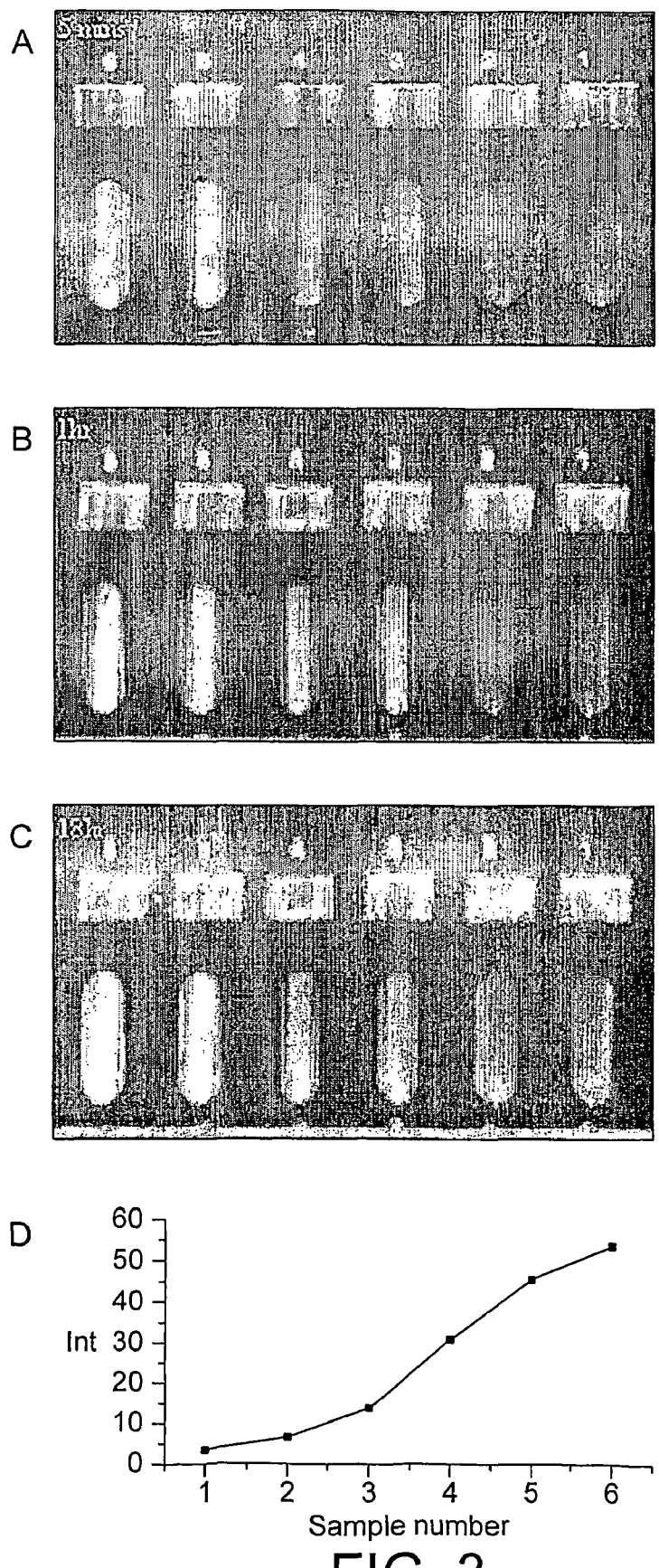

Peptides were prepared at concentrations ranging from 1 to 0.01 mg/ml, depending on the activity of peptide, in deionised. A stock solution of avidin (5 unit per ml, one unit of avidin binds 1 µg of biotin.) was prepared in PBS pH 7.4 buffer. Biotin, from a stock solution of 10 mg/ml prepared in DMSO, was diluted 10000 fold with water to obtain working concentrations of 1 µg/ml. A typical cytolytic assay was performed in a total volume of 2 ml PBS buffer containing calcein liposomes (5 µM lipid) as prepared above. The progress of dye leakage was continually followed using excitation and emission wavelengths of 490 and 520 nm respectively. Peptide of known concentrations-was added at certain time points and the solution was rapidly mixed while continuing to measure signal. For uncloaking the peptide activity using biotin, the additions were made to the buffer sequentially in the order avidin, 2 minute incubation with biotin followed by the addition of biotinylated peptide (44 nM). The mixture was incubated for filter 2 minutes and fluorescence measurement initiated. At selected time points liposomes (7 µM) were added and solution mixed. For the cloaking experiments the additions were essentially the same except no free biotin was added. The avidin concentration was a 1.2 fold excess units to ensure complete cloaking. For evaluating dual trigger switching properties of biotinylated peptide the liposomes (7 µM lipid) in 2 ml of buffer were treated with peptide. (2.8 nM) and fluorescence measured continually. For cloaking experiments and pH arming the peptide solution (2.8 nM) was incubated with a 1.2 fold excess of avidin solution for 3 minutes and the cytolytic assay performed at pH 6.6 and 8. For the uncloaking experiments the avidin was pre-incubated with 11 picomoles of biotin solution. Data is shown in FIG. 2.

Visual Detection of Biotin Analyte

In the control sample, liposomes (4 µM lipid) were added to 1.2 ml solution of peptide (14 nM) pre-incubated with a 1.2 fold excess avidin. Test samples contained biotin at known concentrations. Additions were made sequentially in the order, biotin, avidin, followed by a 1 minute incubation, peptide followed by two minute incubation and finally liposomes. The samples were illuminated from underneath with simple 3 mm wide angle ultra bright blue diodes (RS Components) powered by a 3 Volt battery. Photographs were taken with a standard digital camera after 5 minutes, 1 hr and 18 hrs to visually observe the signal. The actual fluorescence readings after 5 minutes were also recorded using a fluorimeter.

Detection of VTB Epitope and VTEC by pH Arming Liposomal Assay

Figure 5:
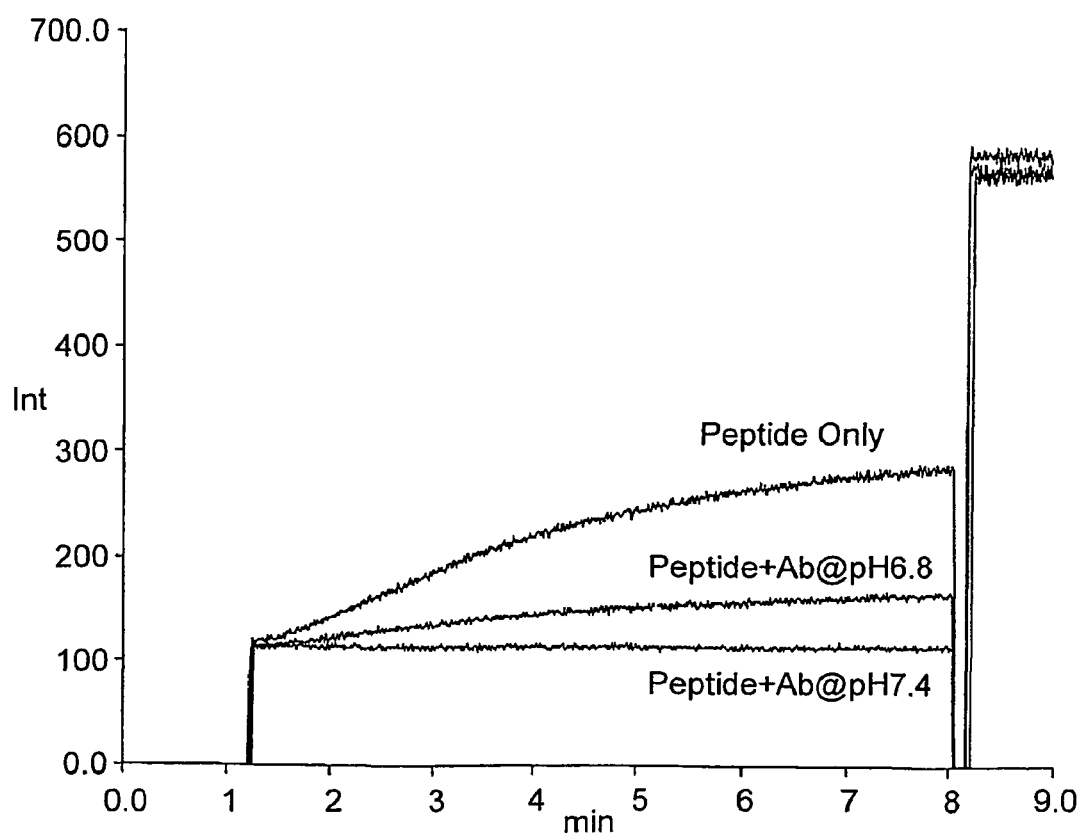

To show the benefit of dual trigger detection the peptide Peptide 2 which has pH responsive profile as shown in FIG. 4 was modified at the cloaking site with a short sequence (ELF-TNR) known to be epitope of verotoxin subunit B (*Infection & Immunology* (1991) 59,750-757) to obtain peptide 6. This peptide was also pH sensitive analogous to its parent sequence Peptide 2. For the detection of VTEC at a pH where peptide is active the conditions of the assay were: 2 ml of assay buffer (140 mM NaCl, 10 mM sodium phosphate buffer containing 5 mM HEPES and 1 mM EDTA at pH 6.8)+3 µl of calcein liposomes (100 nm diameter) were treated with 10 µl of peptide 6 (Screening grade) preincubated (2 mins) with anti-epitope antibody (6 µl of mg/ml protein A pure). FIG. 5 shows the data. The lower curve shows the same experiment at pH 7.4 in presence of antibody. Fluorescence recorded by monitoring emission at 520 nm after excitation at 490 nm. The total release of calcein was achieved by the addition of Triton X-100.

The background apparent at acidic conditions (middle curve) could be maintained low at physiological pH values until measurement was required as shown in FIG. 5. It is thus clear that detection would only be possible below physiological pH. The following examples show that the peptide liposome complexes can be unarmed and analytes detected at pH 6.8.

Figure 6:
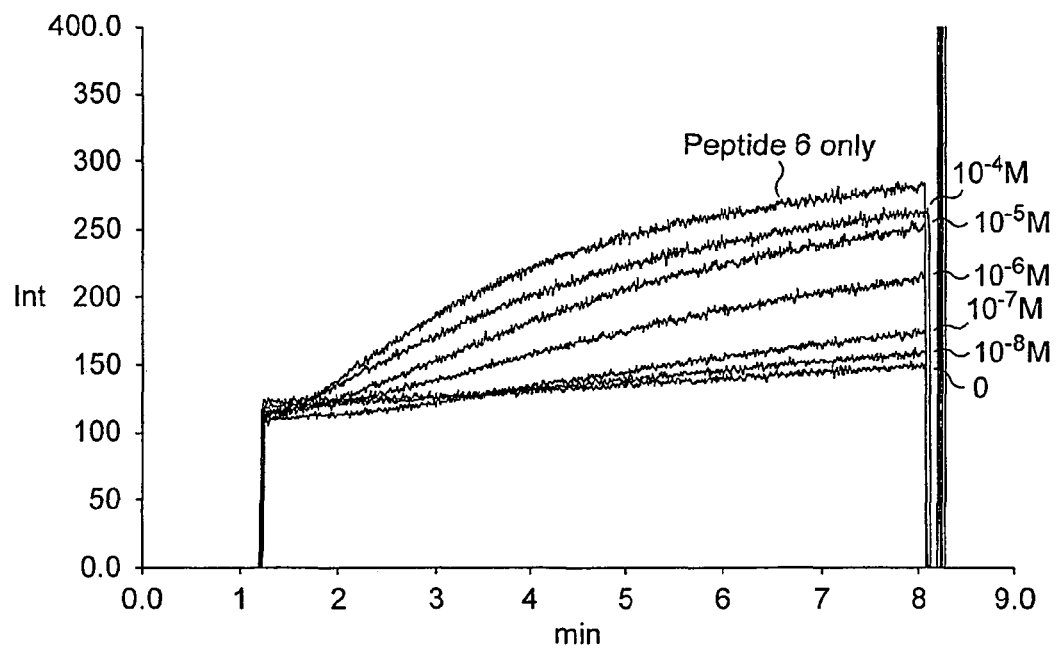

VTB epitope could be detected by release of calcein from 3 µl of liposomes (100 nm) by peptide 6 in the presence of free epitope (ELFTNR) competing for anti-epitope antibody. The assay was performed in 2 ml of buffer (140 mM NaCl, 10 mM sodium phosphate, 5 mM HEPES and 1 mM EDTA). Peptide 6 and free epitope were allowed to compete for 6 µg antibody prior to addition, This data is shown in FIG. 6.

Figure 7:
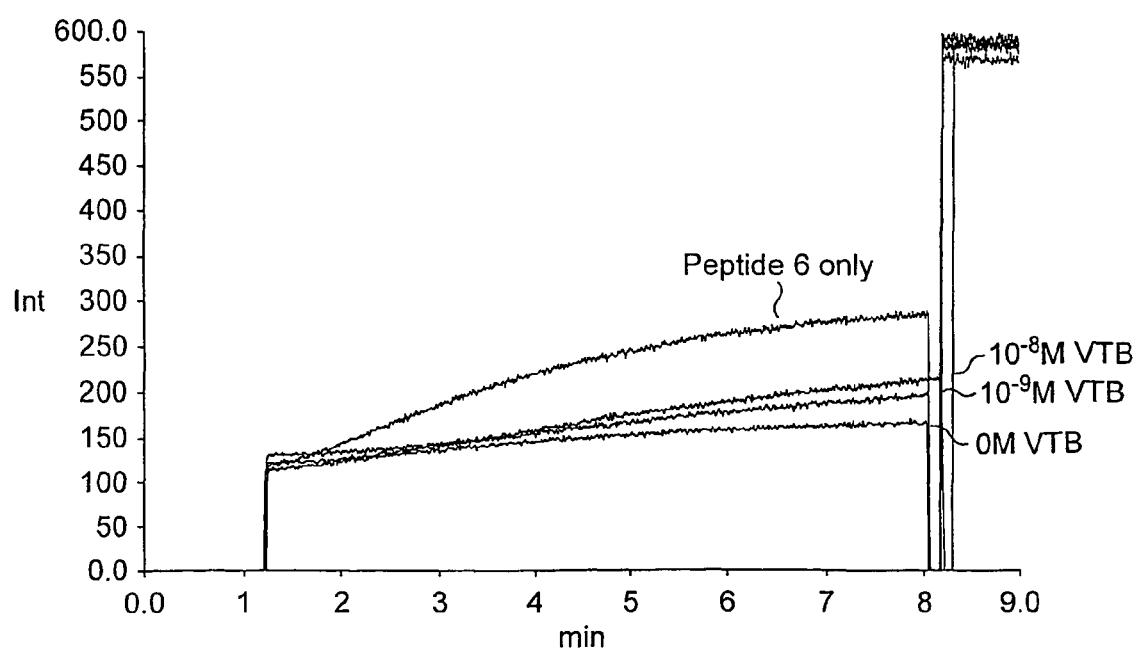

VTB subunit could also be detected similarly using following conditions. Release of calcein from 3 µl of liposomes (100 nm) by peptide 6 in the presence of VTB subunit competing for anti-epitope antibody. VTB and antibody were preincubated for 3 minutes before the addition of peptide 6. The assay was performed in 2 ml 140 mM NaCl, 10 mM sodium phosphate buffer pH 6.8 containing 5 mM IEPES and 1 mM EDTA with detected concentrations of epitope indicated on the trace. Data is shown in FIG. 7 with detected concentrations of VTB indicated on the trace Liposome-Peptide Integral Complex:

A fatty acid incorporated on the N-terminal of peptide anchors the sequence with liposomes to form integral complex which can then be used as single stable reagent that can be triggered to release the contents-of the liposomoes when the pH is ideal (i.e physiological 7.4) or acidic (e.g 6.2). In the first instance we prepared the liposome-peptide complex at a predetermined ratio of lipid-to peptide (30:1) in pH 8 buffer using peptide 10. The ratio was pre-determined by carrying out series of lytic profiles at different concentrations and pH values to reach conditions whereby little or no lysis was observed at pH 7.4 while significant release was evident at acidic values. The complex between liposomes and peptide was formed by adding peptide to 2001 µl of 10 mM NaP containing 140 mM NaCl, 1 mM EDTA, 5 mM Hepes pH 8 buffer, containing 100 µl of calcein encapsulating liposomes. The mixture was incubated for 20 mins to form the complex prior to use. In order to ascertain that the lysis is occurring due to the formation of complex and not as the action of the peptide per se it was essential to purify the liposome-peptide complex. The peptide to lipid ratio in this complex is 1:30. The complex was applied to a Sepharose CL-6B column. Fractions corresponding to liposomes were collected as clearly visible to the eye. Aliquots of these fractions were then tested for lytic activity at acidic and physiological pH values. The key aim was to establish that the peptide is liposome associated and would thus be eluted with liposome fraction in the void volume. We used 100 µl complex (a column purified fraction) and followed the release of Calcein at two different pH values.

Figure 8:
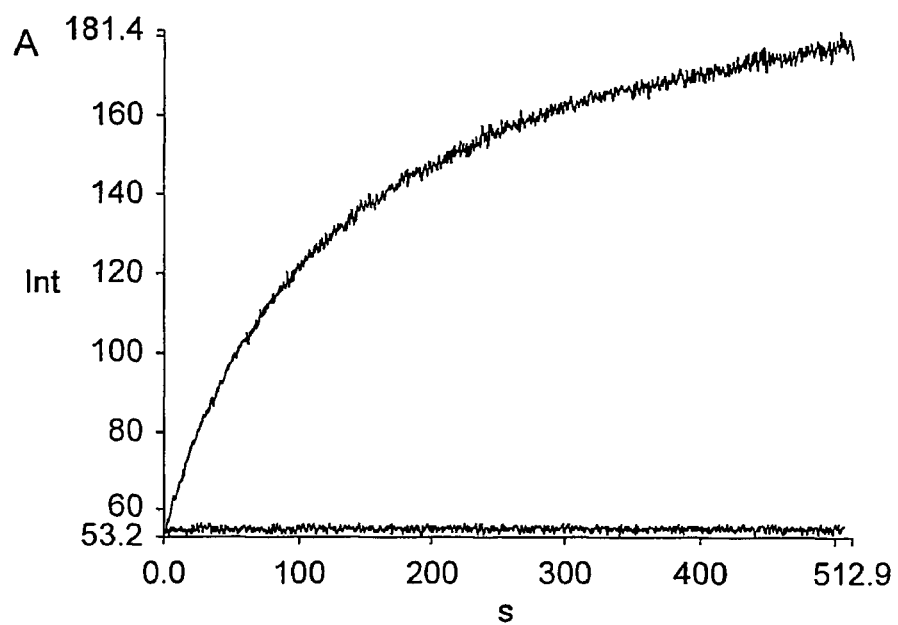
Figure 8:
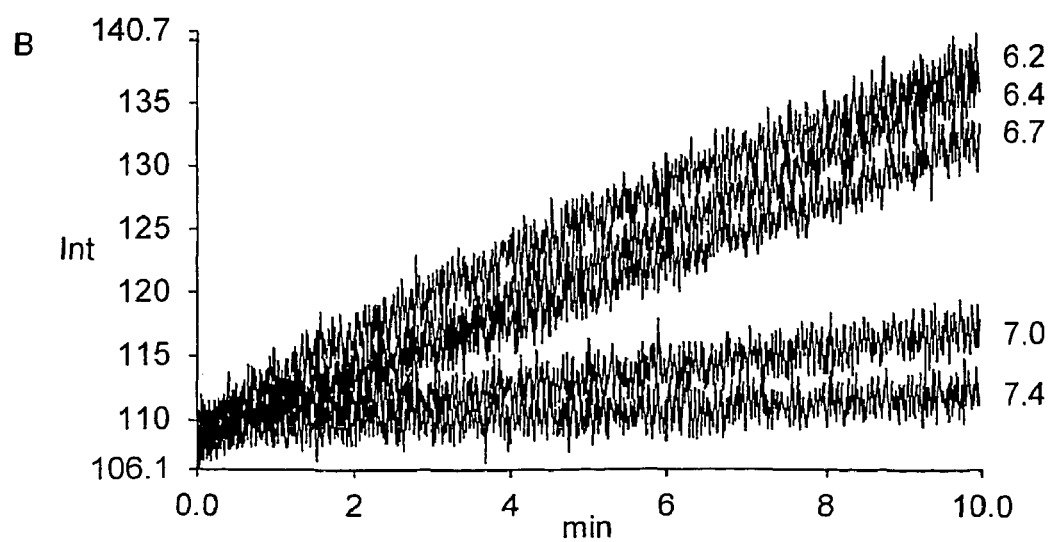
Figure 8:
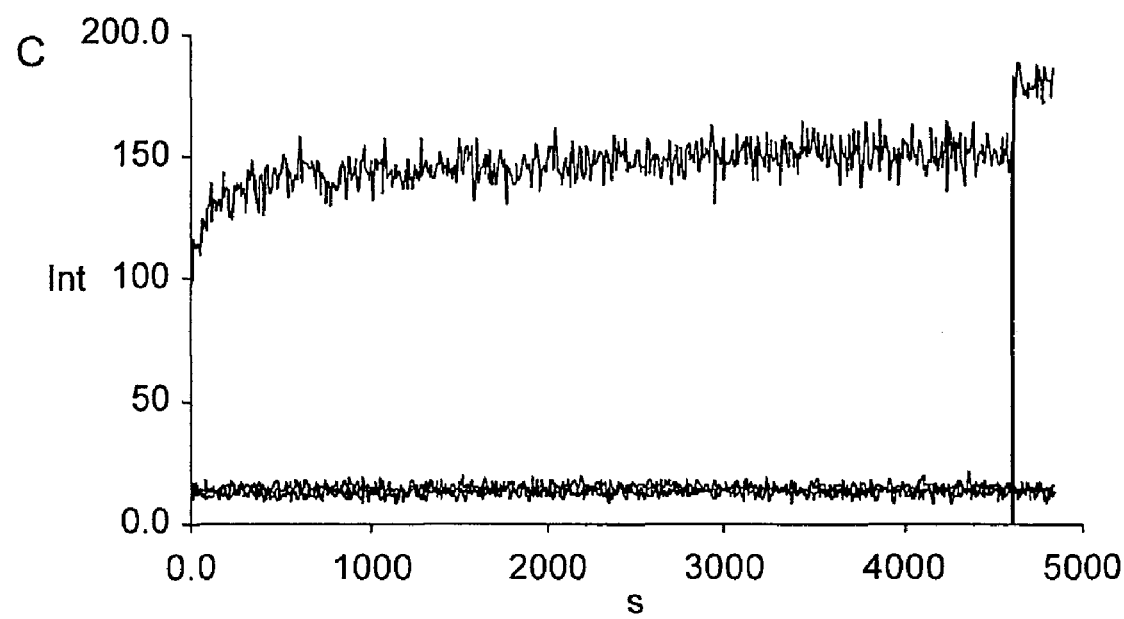
Figure 8:
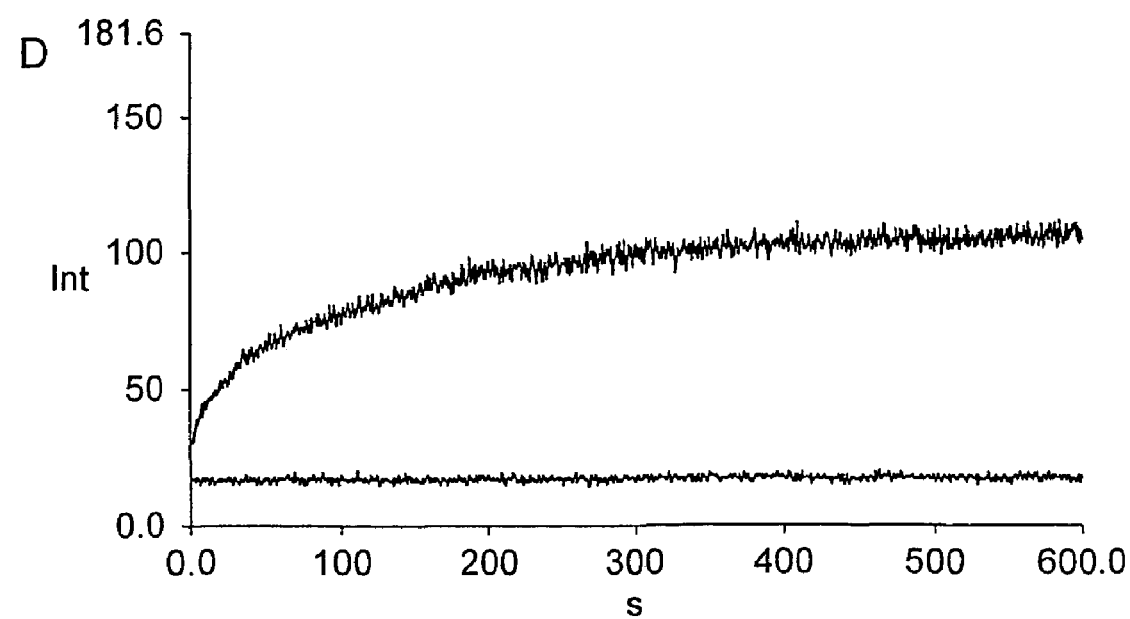
Figure 8:
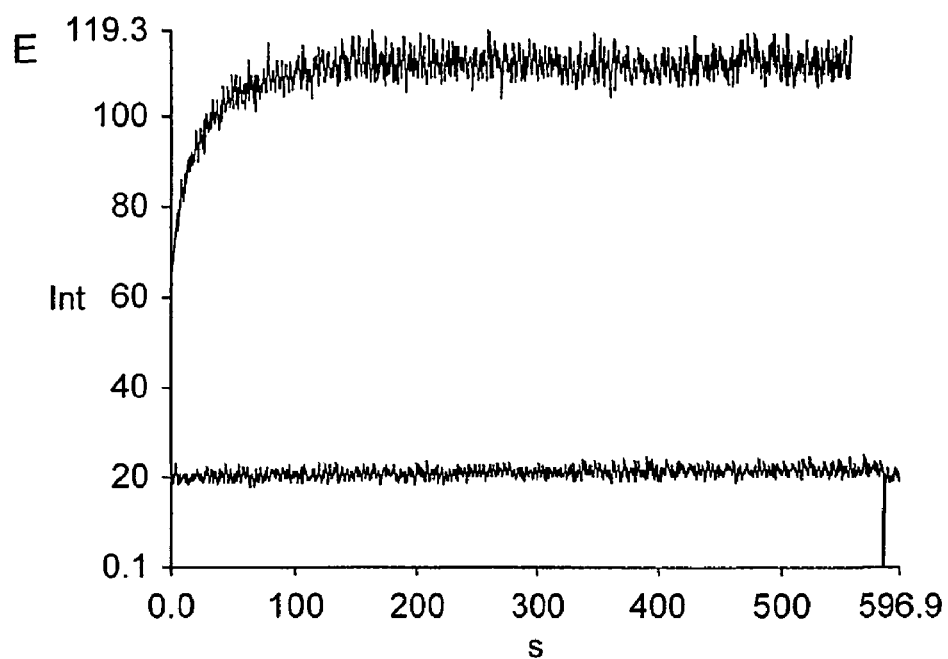
Figure 8:
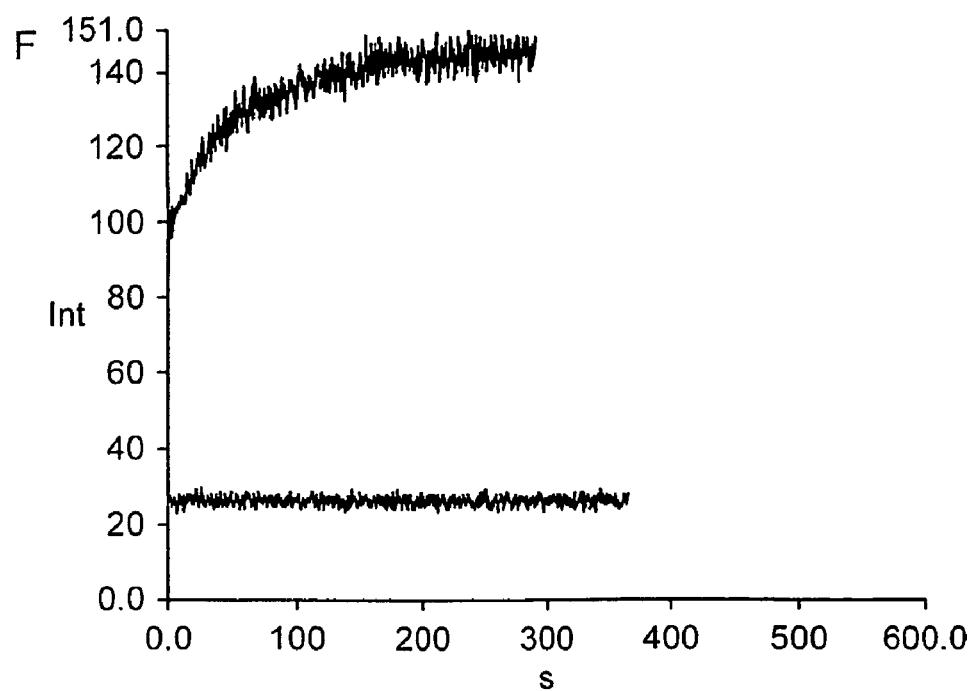

FIG. 8 Shows:

FIG. 8A. Trigger of complex after sepharose CL-6B column in buffer Specifically, 100 µl Liposome+peptide complex after elution through Sepharose-6B column equilibrated by NaP buffer at pH 8.01 was added to a final volume of 2 ml NaP Buffer (10 mM Sodium Phosphate+150 mM NaCl+5 mM Hepes+1 mM EDTA) at two different pH concentrations. Upper curve pH 5.8. Lower curve pH 7.4.

FIG. 8B Purified Peptide(P9)-Liposome Complex Conditions 2 ml buffer (10 mM Na phosphate, 140 mM NaCl, 1 mM EDTA, 5 mM HEPES)+50 µl purified complex. Lipsomes used were 50 nm extruded. Curves top to bottom are pH 6.2, 6.4, 6.7, 7.0, 7.4

FIG. 8C. Lytic Assay of Complex

Complex 20 µl liposomes+60 µl pH 8 buffer+20 µl peptide (0.1 mg/ml) prepared and used within 2 minutes. 10 µl was added to each of the cuvettes containing 2 ml buffers. Top curve pH 6.2 (triton was added towards the end indicated by sharp dip in fluorescence to check full lysis), the lower curve is at pH 7.4. Samples measured simultaneously.

FIG. 8D Stability of Complex (Used for in Vivo Studies) 20 Minutes from Preparation 5 µL of complex in 2 ml of buffer tested 20 minutes after preparation. Upper curve pH 6.2, Lower curve pH 7.4.

FIG. 8E Stability of Complex (Used for in-Vivo Studies) 1.5 hr from Preparation

5 µL of complex in 2 ml of buffer tested 5 hrs after preparation. Upper curve pH 6.2 and lower curve pH 7.4.

FIG. 8F Stability of Complex (Used for in-Vivo Studies) 24 hrs Minutes from Preparation 5 µL of complex in 2 ml of buffer tested 24 hrs after preparation curve pH 6.2, Lower curve pH 7.4.

Data in FIG. 8A shows that the liposome-peptide complex remains intact and shows pH responsive properties. During purification of the liposomes we noted some Calcein on top of the column. This indicates that there is some leakage of the dye when complex is formed. Upper trace at pH 5.8 peptide shows the acid triggered release while the trace at pH 7.4 shows little or no release indicating a stable complex.

Complex formed by another peptide (peptide 9) also showed (FIG. 8B) that triggering properties are retained after purification. For this peptide a different peptide to lipid ratio (1:300) was used.

From the above experiments it was conclusive that the peptides remain liposome-associated to cause release of payload.

The data in the above traces was for regular Calcein liposomes. For in vivo applications we incorporated another dye DiI into liposomes to assist quantification. These liposomes showed adequate triggering properties with the peptides. The data in FIG. 8C shows triggering of the peptide 9 (table 1) with these liposomes. Using several trial and error ratios of liposomes, peptide and buffer the most optimised complex required 20 µl liposomes, mixed with 60 µl pH 8 buffer to which 20 µl of peptide (0.1 mg/ml) is added. The traces in FIGS. 8D, E, F shows stability of the complex by retention of the pH triggering of properties as tested 20 minutes, 5 hrs and 24 hrs after preparation.

Stable complexes without purification can be produced by optimising peptide to lipid ratio and concentration highlighting the reality of producing single reagent formulation.

Figure 9:
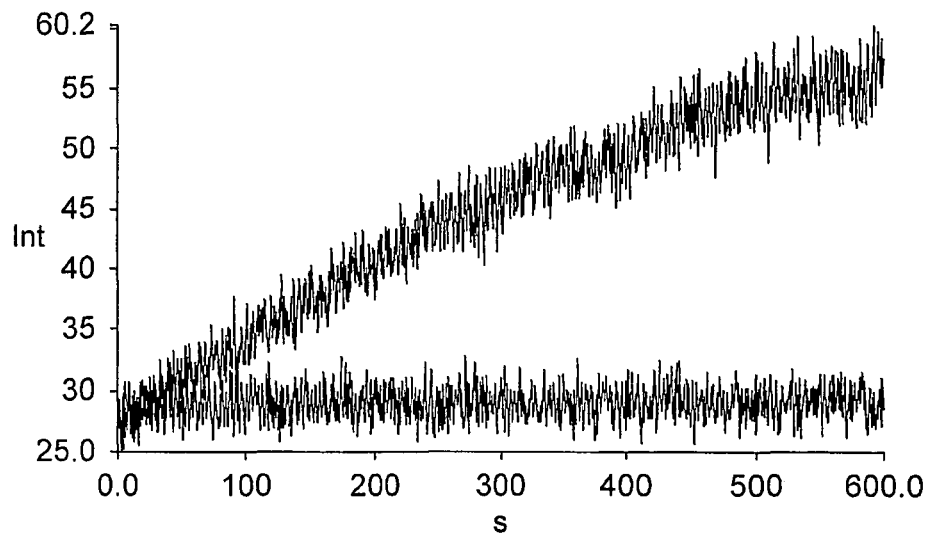

Other peptides can also form complexes which trigger in acidic media (upper curve). For instance shown in FIG. 9 is the data for peptide 1.

Alternatively the complex formed could be gel-filtered to remove unattached peptide and an aliquot of eluant tested to show activity. The formation of complexes requires a careful study of lipid to peptide ratio. However once conditions are determined, the armed complexes of this type can be scaled up and used to release payload at acidic regions such as tumour. The binding of avidin to the biotinylated peptide could also be used to switch off the activity for added fidelity. It is also possible to accumulate these complexes at target sites and then modulate the pH to release payload locally. Methods of modulating pH have previously been reported (*Cancer Res* 1982, 1505-1512 & *Cancer Res* 1994, 3785-3792).

Figure 10:
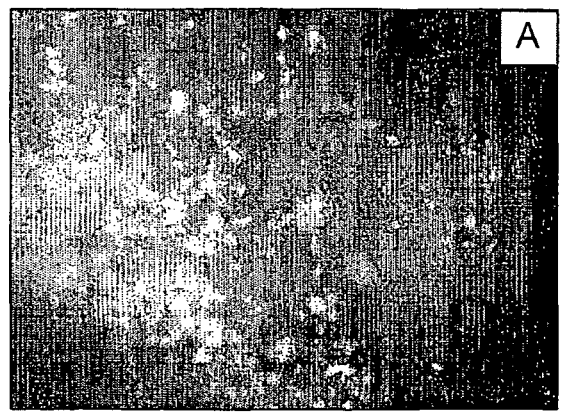
Figure 10:

Similar methodology could be used for in vivo imaging of tumours whereby the payload is a marker or diagnostic reagent sequestered inside liposomes. For instance, when using the dye calcein, the pH released dye would be detected by increase in green fluorescence. FIG. 10 shows data to illustrate this effect with pH armed complex of the peptide with calcein liposomes. Complex was prepared from biotinylated peptide (1) by adding 10 µl of pH 8 buffer to 41 µg of peptide to which was added 150 µl of Hposomes encapsulating calcein. The complex was incubated briefly and 100 µl was injected via the tail vein into mice with implanted tumours. The control mice were given equivalent levels of untreated liposomes. Using the dorsal window chamber model (*Biophysics*. 1997,1785-1790 & *Nature Biotechnology* 1999,17,1033-1035,) with implanted tumours (Rif-1 allografts) direct in vivo examination of the calcein in and around the tumours was made by fluorescence microscopy and computer controlled time-lapse images. Photographs shown in FIG. 10. illustrate that the armed complex liposomes shows an intense image (B) relative to the control liposomes (A) indicating that the complex has been unarmed by the tumour pH. Note that many tumours in animals and human, Rif-1 being one example, have an ambient pH that is slightly lower than that of normal tissue (*Science* 1980, 210, 1253-1255 & *Cancer Res* 1989,4373-4384). This pathophysiological feature of tumours may be used for cancer detection. Thus unarming the complex which triggers below but close to physiological pH causes the release of dye almost immediately. This way the armed complexes can be used for in vivo detection of disease and particularly for the detection of cancer. Similarly, if the payload was combination of calcein dye and anticancer drug it would be possible to detect and treat with same formulation offering major advantages for diagnosis and treatment.

Phosphorylation of the Peptide or Complex:

The peptide or complexes of the invention can also be armed by including sequences or chemical modifications that can be cleaved by enzymes. This is illustrated using phosphorylated peptide. The peptide or complexes can also be phosphorylated to achieve inactivity. De-phosphorylation and lowering of pH then provides controlled release of payload.

Peptide 12 (Table 1) was synthesised manually by solid phase Fmoc (9-fluorenylmethoxycarbonyl) chemistry using 0.25 mmole of Rink amide resin as the solid support. The following standard Fmoc-amino acid side chain protections were used: Glu: t-Bu; His: trityl; Arg: Pmc. For serine Fmoc-O-benzyl-L-phosphoserine obtained from Calbiochem-Novabiochem (UK) was used. The Fmoc protections were removed by treatment of the resin with a solution of piperidine in dimethylformamide (20%, v/v), respectively. Protected Fmoc-amino acids (NovaBiochem) were activated at their carboxyl groups using 3 equivalent (eq) of amino acid, 3 eq benzotriazole-1-yl-oxy-tris-(dimethylamino)-phosphonium hexafluorophosphate (BOP), 3eq N-hydroxybenzotriazole monohydrate (HOBt) and 6 eq of DIPEA (N,N-di-isopropylethylamine). The activated Fmoc-amino acid was coupled to the free amino terminus of the elongating peptide on the resin. Completion of the each acylation steps was monitored by the Kaiser test. Recoupling was performed if the couplings were incomplete. Myristic acid was coupled in the same manner as amino acid. The phosphopeptide as the C-terminal amide was cleaved from the resin using 94% TFA, 2.5% water, 2.5% ethanedithiol and 1% triisopropylsilane (Aldrich). The crude peptide was purified on a C-4 reverse phase semipreparative (Vydac 250×4.6 mm cm) column Elution was accomplished using a 30 min gradient of 10-100% aqueous acetonitrile containing 0.1% trifluoroacetic acid (TFA) at a flow rate of 8 ml/min. The main fraction was collected and lyophilised.

Figure 14:
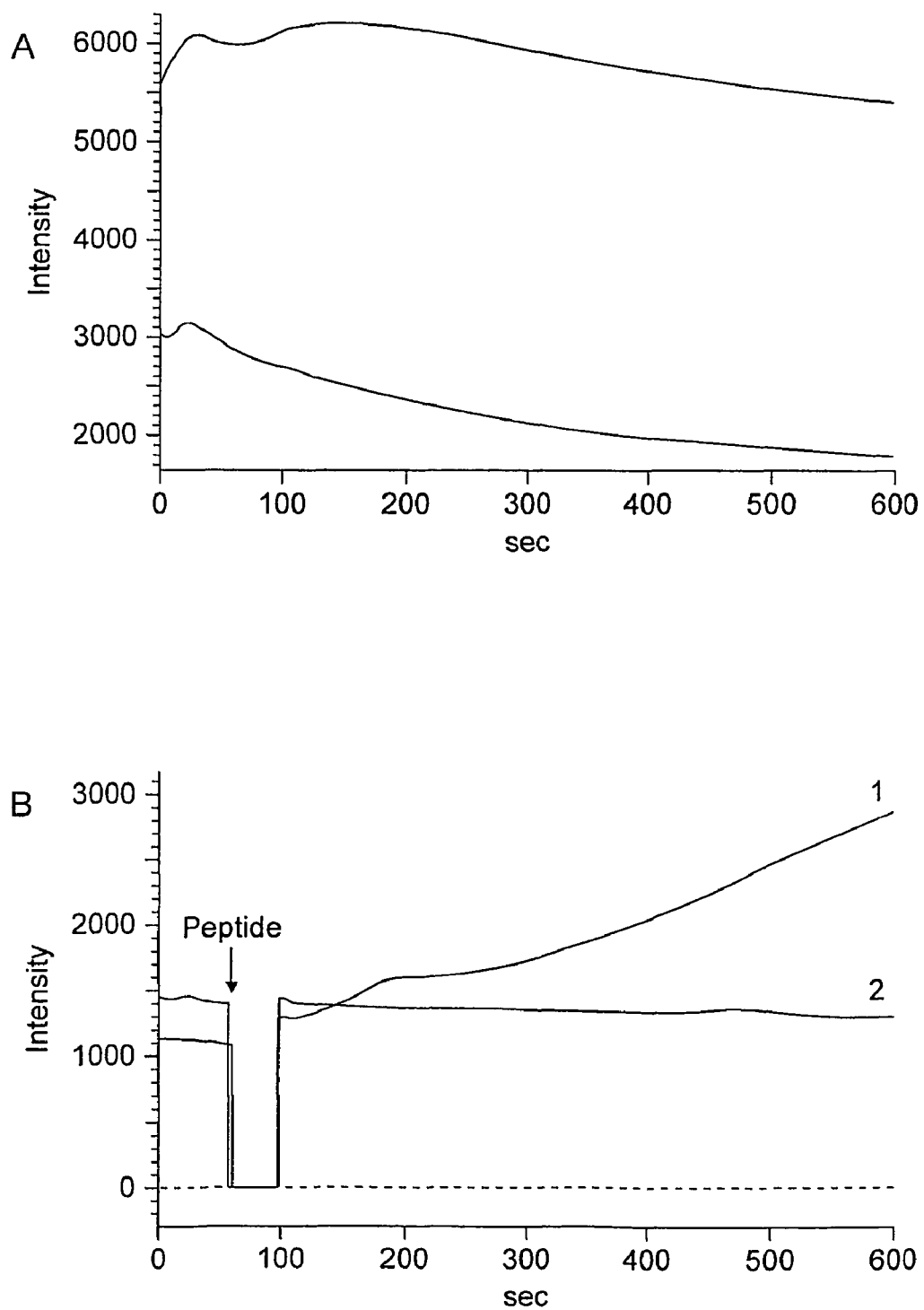
FIG. 14A is a graph showing lysis of calcein liposomes with peptide 12 in the presence (upper curve) and absence (lower) of alkaline phosphates.
FIG. 14B is a graph showing activation of a peptide by an enzyme (alkaline phosphatase) giving calcein release at acidic pH. Curve 1 represents the enzyme treated peptide whilst curve 2 represents non-treated peptide.

Alkaline phosphatase (bovine intestinal mucosa) obtained from Sigma was used for dephosphorylation of peptide at the serine phosphate. A 10 µl of Peptide solution (0.01 mg/ml) was added to 2 ml of 10 mM HEPES buffer at pH 6.8 and 10 units of alkaline phosphatase added. After allowing 10-minute incubation for dephosphorylation calcein liposomes (5 µM lipid) were added and fluorescence intensity recorded using wavelengths of 490 nm for excitation and 520 nm for emission. Control experiment was conducted in the absence of alkaline phosphates. FIG. 14A compares the traces showing substantial dye release (upper curve) in the presence of alkaline phosphatase compared to low release (low release) in the absence of enzyme. Thus the enzyme treatment yielded the dephosphorylated peptide resulting in activation of the peptide under mildly acidic conditions 3 µl of 0.1 mg/ml of peptide 12 (table 1) was incubated for 10 minutes with alkaline phosphatase in 20 µl 10 mM Tris-HCL pH 8 buffer. This was then added (see arrow on FIG. 14B) to 2 ml PBS pH 6.6 buffer containing 3 µl of calcein liposomes (3 mg/ml lipid concentration). Fluorescence was recorded as a function of time with excitation and emission wavelengths of 490 nm and 520 nm respectively. A similar experiment was carried out in the absence of alkaline phosphatase. The data in FIG. 14B clearly indicates that the enzyme treatment yielded the dephosphorylated peptide resulting in release of the dye by the activation under mildly acidic conditions (curve 1) compared to no or little rate increase in the non-treated (curve 2) sample.

Many tumours are known to have either elevated proteolytic levels or to produce specific enzymes. A protease-specific sequence for instance cysteine or serine protease sensitive sequences could be attached to the peptide which render the peptide or complexes inactive and cleavage of this sequence along with low pH activates the peptide to release payload. There are several protease specific sequences, which could be used in this manner. For instance, peptide substrate sequences cleaved by a prostate specific antigen are known. Other proteolytic sequences for enzymes like Elastase, thrombin and endosomal lysosomal enzymes such as cathepsins B,D,H and L are also known. In addition to this suitable proteases could be targeted to cells or tissues.

pH Arming DNA Delivery

Figure 15:
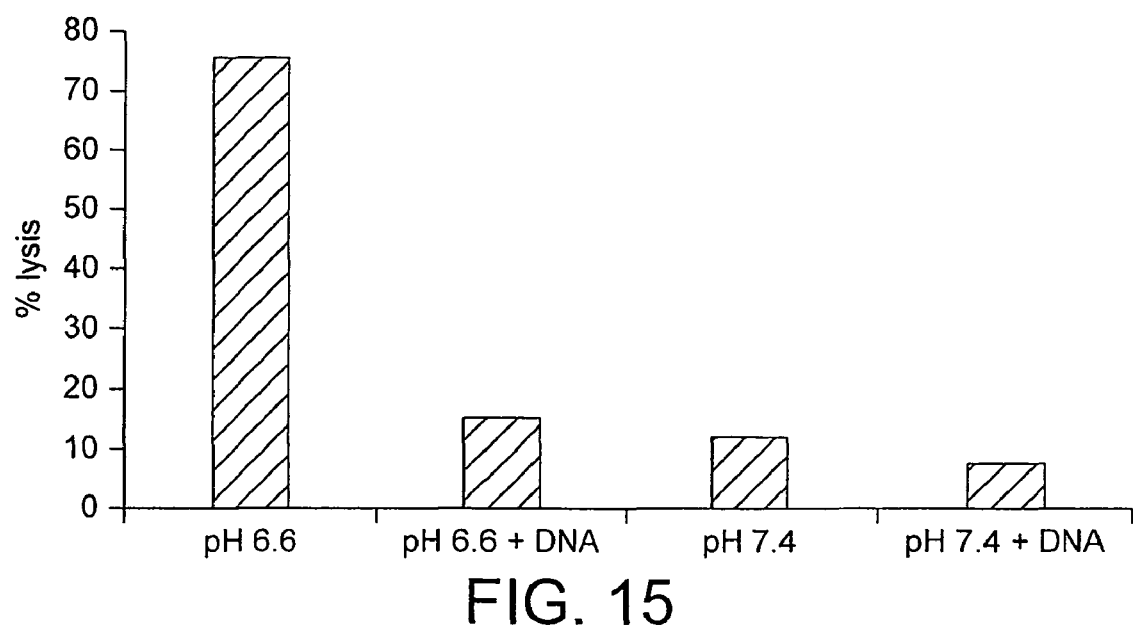
FIG. 15 is a graph showing relative lysis of calcein liposomes at acidic and physiological pH in the presence and absence of DNA.

Peptide 13 in table 1 was used to demonstrate cloaking peptide activity with pH and DNA binding. Calcein liposomes containing (5 µM lipid) were added to 2 ml phosphate buffered saline containing the peptide (0.4 µM) and the fluorescence recorded. This was carried out at pH values of 6.6 and 7.4. The fluorescence intensity indicative of leakage after five minutes was expressed as a % of lysis obtained with 10 µl of 10% Triton-X100. the latter taken to represent 100% lysis. The experiment was repeated whereby the peptide was pre-condensed with calf thymus DNA (Sigma) at charge ratio to give minimum lysis at pH 7.4. The results in FIG. 15 show that the peptide is activated by acidic pH when no DNA is present. It can be concluded that DNA binding results in substantial inactivation of the peptide. Thus the DNA condensate of the peptide would require both the de-condensation and slightly acidic conditions to cause lysis. Cloaking of peptides with DNA binding and pH has obvious advantages when delivering genes via the endosome route where low pH is encountered. A combination of highly anionic region (towards the N terminal end of peptide 13 table 1 residues LEAALAEALEAL) and highly cationic region (the c terminal end of peptide 13 table 1, residues RRRRQQ,) within the same polypeptide sequence is critical to this fuction.

To assess condensation of DNA to peptide and its effect on cytolytic activity, assays were performed at several different pH values and at different peptide to DNA ratios. Peptide appears to be inactive at physiological pH bound to DNA while activity is regained at acidic pH where the DNA is substantially dissociated. The peptide or complexes have a property of retaining high basic character on one end which is essential for DNA binding while retaining highly acidic character on the other half of the molecule which is critical for pH switching.

Drug Delivery

The peptide was shown to be triggered closer to physiological pH and this could be used for delivery drugs to acidic areas. The peptide has a fatty acid attached which could be used to form complex with drug containing liposomes. These liposomes have therapeutic importance. The peptide liposome assemblies could be targeted to cells or accumulated in the tumours whereby binding to a specific marker and a change in pH effects specific release of the drug. Alternatively, the complexes may trigger drug release by simple pH change. Delivery to tumours have clinical relevance as some tumours are shown to be acidic compared to pH of normal tissue. In order to improve delivery of drugs to cancer cells the peptide could be inactivated by attaching protease specific sequence which would be cleaved in the tumour. However, to control the activity further the peptide would then require acidic pH to release liposome contents. This way damage to any normal tissues which may have traces of the same protease present could be minimised by very biospecific release at the target site.

Figure 11:
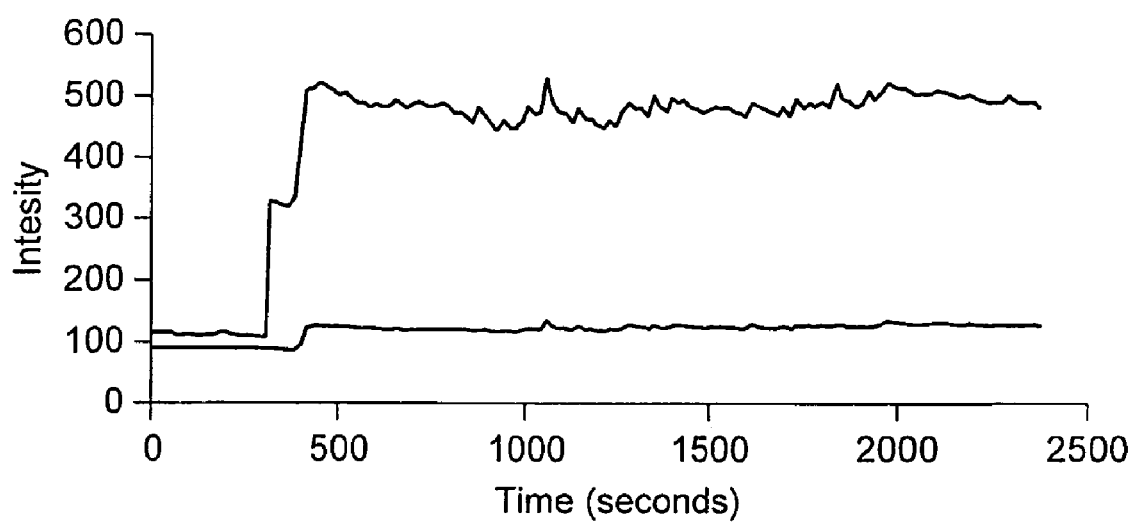

Liposomes encapsulating Calcein (120 mM) and with label DiI (the dye to lipid ratio was around 100 µg dye: 100 mg PC) were used. C3H syngenic mice 8-10 weeks old weighing 20-25 g were used. Subcutaneous tumour was implanted using KHT cells ($5 \times 10^6$ cells/animal) on the dorsal side after shaving the mice. Typically 200 µl of peptide liposome complex (100 µl of dual dye liposomes+100 µl of peptide 0.1 mg/ml) were administered intravenously per mice and tumours excised 3 hrs post inoculum. The tumour was removed aseptically and kept in PBS pH 8.0 buffer and thin sections (160 µm-200 µm) were cut on the slicing machine, and examined under a fluorescence microscope. The pH of the buffer was modulated by adding 400 µl of NaP buffer pH 5.8 while simultaneously removing 400 µl of pH 8 buffer. Changes in fluorescence intensity were recorded. The state of liposome peptide complex is then determined, whether intact or lysed by measuring fluorescence in tissue slices before-and after incubation in acidic buffer. The increase in fluorescence in the acidic buffer indicates the quantity of liposomes that were still intact and able to respond at the time of sacrifice. FIG. 11 shows that the liposome complexes with peptide 9 were able to trigger release of calcein in this ex vivo experiment. Upper curve shows fluorescence intensity of Calcein dye while the lower curve shows fluorescence intensity of DiI dye. A similar demonstration was then made in vivo as described below.

For the in vivo experiments the tumours were grown in the dorsal skin of C3H mice. Window chamber measurements were carried out on RIF tumour allografts. To achieve acidification of tumour at the time of liposome injection a portion of animals were pre-treated with MIBG/glucose. Tumour bearing mice were given an intra-peritoneal injection of MIBG to lower tumour pH, at a dose of 40 mg/kg MIBG (meta-iodobenzylamine, 0.01 ml/g body weight of a 4 mg/ml solution in PBS) and 1.5 g/kg D-Glucose (0.01 ml/g body weight of a 0.15 g/ml solution) given one hour prior to injection of the liposome preparation. The mice were then given the agent (0.1 ml of liposomes+0.1 ml of PBS pH 8) or peptide-liposome complex (0.1 ml+peptide in. PBS pH 8) in total volume of 0.2 ml by a tail vein injection. The control or peptide-liposomes were injected into the tail vein while the mice were on the microscope stage. The computer-controlled imaging system was instructed to begin acquiring time-lapse images in both fluorescence channels (Calcein and DiI). Images were acquired at a rate of 4 to 12 images per minute. Changes in fluorescence were monitored continuously. DiI intensity was measured using a Texas Red filter set (excitation 560/dichroic cutoff 595/emission 620). Calcein intensity was measured using a fluorescein filter set (480/5.05/520). The release rate of calcein dye from liposomes was determined by a dual fluorophore ratiometric method. Automated data acquisition routines were written using imaging/instrument control software (Metamorph, Universal Imaging). These routines control the operation of the lamp filter wheel and shutter for control of fluorescence excitation, operation of the cooled scientific CCD camera for image acquisition, and analysis of images. The following calculations are done in real time: subtraction of background intensity levels; calculation of mean, maximum, and variance of fluorescence intensity; relative change in intensity for each fluorescence channel; and ratio of intensities at different wavelengths. Release kinetics are recorded in raw form as intensity versus time for each of the two fluorescence channels (green/calcein/contents and red/DiI/liposorne). A normalised kinetic plot is obtained by dividing the contents signal by the liposome signal.

$$\text{Normalised Release} = \frac{\frac{I_{contents}(t)}{I_{contents}(t_0)}}{\frac{I_{lipo}(t)}{I_{lipo}(t_0)}}$$

Or $$\text{Normalised Release} = \frac{I_{contents}(t)/I_{contents}(t_0)}{I_{lipo}(t)/I_{lipo}(t_0)}$$

The raw intensity vs time data collected during the first 30 minutes after injection was converted into a ratio of calcein fluorescence to DiI fluorescence intensity, and normalised so that the ratio immediately after injection (i.e., when the step increase in tissue fluorescence occurs) is taken to be 1. Consequently ratios higher than 1 are taken to indicate release of Calcein.

A rapid jump in both DiI and calcein fluorescence was observed corresponding to the filling of the vascular compartment of the tissue. Subsequently, a slow increase or decrease of DiI fluorescence occurred, reflecting the combined effects of plasma clearance (tending to reduce intensity) and extravasation into interstitial space or uptake into cells (tending to increase intensity). Calcein intensity always exhibited a continued increase, reflecting the release and de-quenching of calcein from liposomes.

Figure 12:
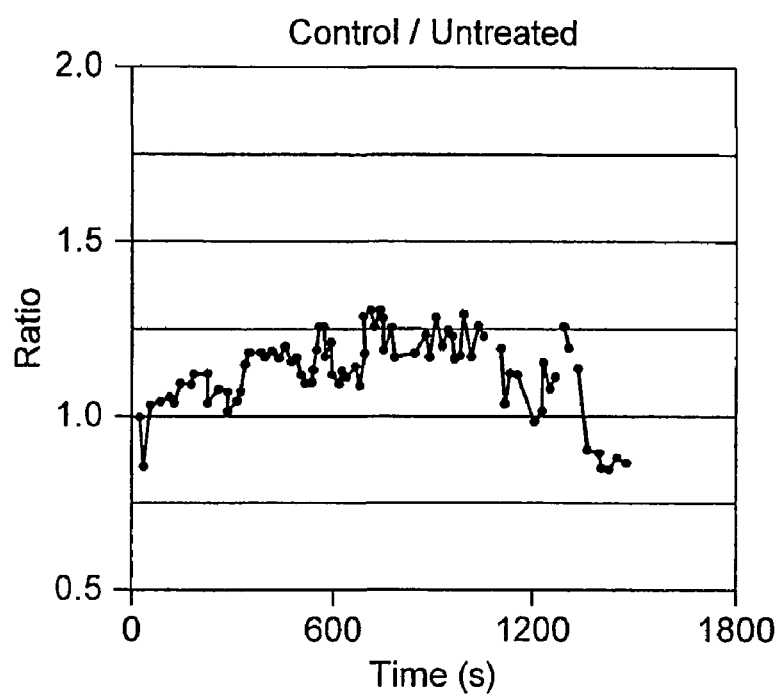
Figure 12:
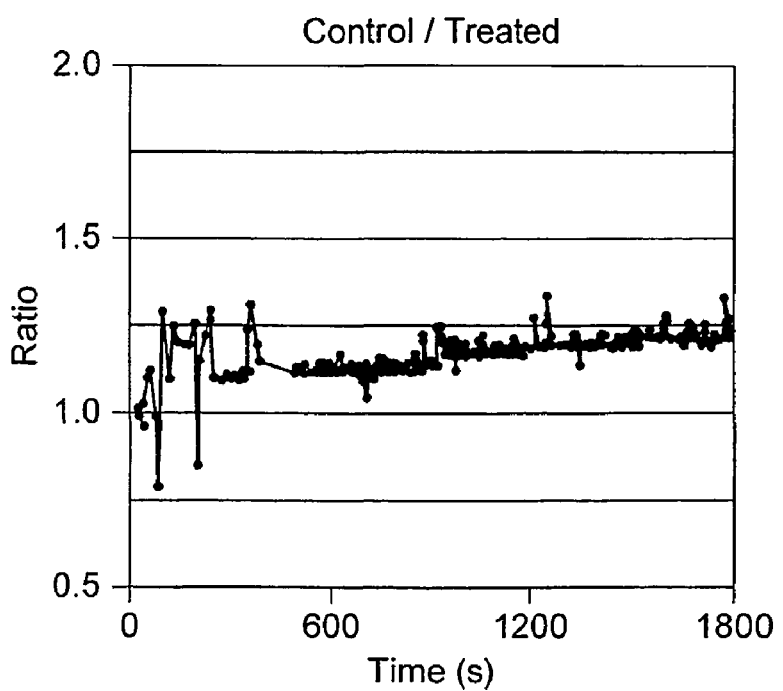

FIGS. 12 shows the normalised change in calcein intensity for the DiI labelled Control liposomes in untreated (upper) and MIBG/glucose-treated (Lower) tumour tissue.

Figure 13:
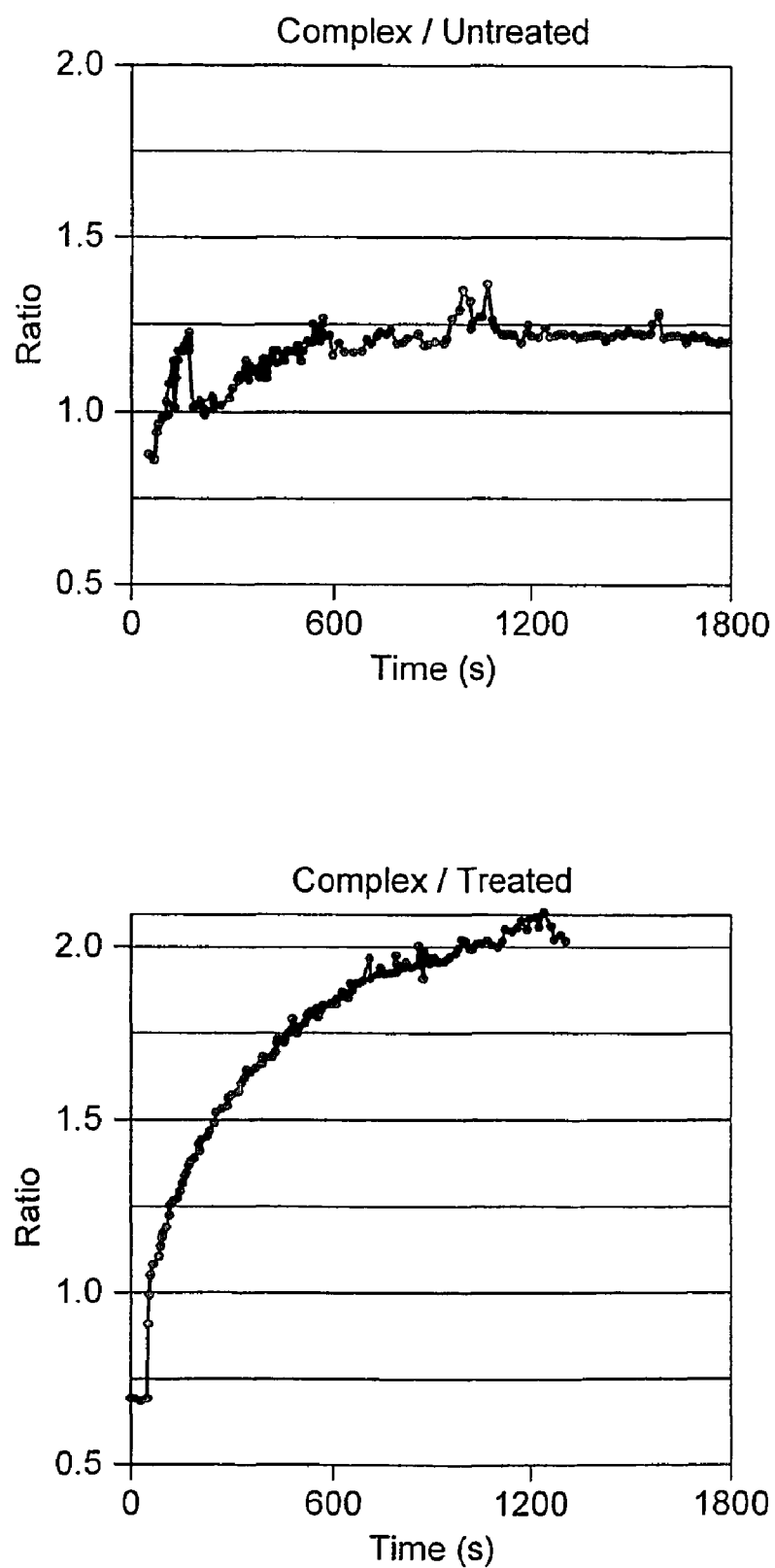
FIG. 13 is a graph showing the release of dye from liposomes in a tumour.

FIGS. 13 shows the normalised change in calcein intensity for the DiI labelled Peptide liposome complex in untreated (Upper) and MIBG/glucose-treated (lower) tumour tissue. The peptide used was peptide 9 in table 1. MIBG/glucose treatment was administered 3 hours prior to liposomes.

The rate of calcein release, as indicated by the normalised calcein:DiI ratio, remained at ~1.25 or below for the control liposomes and for the peptide-liposome complex in untreated control tumour. However, the ratio consistently exceeded 1.5 for complex in MIBG/glucose treated tumour and usually approached 2 or higher. Compared to the other groups, the tumours receiving peptide complex and MIBG treatment exhibit a significantly higher peak normalised calcein:DiI ratio ($p<0.001$ by unpaired t-test). The window chamber data provides strong evidence for release of payload (calcein) in response to tumour pH. The peak normalised ratio indicates the change in calcein fluorescence due to release from liposomes. A value of 1 indicates no change. Compared to a value of 1.33, a value of 2 corresponds to a 3-fold greater change.

Data shown in earlier example (FIG. 10) used a different peptide (peptide 1) which was shown to trigger closer to physiological pH than peptide 9. As illustrated in FIG. (10) significant release of payload was noted even in untreated (No MIBG/glucose) mice.

Measurements of tumour pH were undertaken to show that the pH of this tissue was acidic and in the triggering range of complexes. For pH measurements, a needle-type combination pH microelectrode in a 20G needle was used (tip diameter 0.89 mm; model 818; Diamond General, Ann Arbor, Mich.). These pH electrodes contained an internal reference electrode. The animals were anaesthetized and pH measured by inserting the needle tip probe into tumour. For each tissue type, 15 to 20 readings were taken. We compared microelectrode pH measurements in tumour tissue of untreated and MIBG/glucose-treated mice. The aim was to test whether the in vivo tumour models are acidic and that the MIBG/glucose pre-treatment protocol induces an additional shift toward lower pH. The untreated animals showed mean RIF tumour pH value of 6.8 while the treated animals showed pH value of 6.6. We made similar measurements in KHT tumours. Again, tumour pH was acidic typically in the range 6.64 to 6.69. MIBG treatment made little difference in this tumour model.

Multi-Triggering

It is obvious to those skilled in the art that parameters used for switching peptide activity could be combined to achieve multi-triggering which does not necessarily involve low pH. These parameters also fall under the scope of our invention. For instance a protease sensitive peptide could be rendered inactive by binding to another receptor or antibody or ligand binding protein or DNA whereby proteolytic cleavage and freedom from the bound protein is required to achieve activation. Indeed in the case where the peptide is pH active all three parameters will need to be met before a trigger is evident.

The invention claimed is:

1. A peptide fatty acid conjugate capable of forming a complex with a liposome, the peptide fatty acid conjugate selected from the group consisting of SEQ ID NOS:1, 2 and 6.

2. A composition comprising:
 a peptide fatty acid conjugate bound to a liposome having a therapeutic or diagnostic agent encapsulated therein, wherein the peptide fatty acid conjugate is selected from the group consisting of SEQ ID NOS:1, 2 and 6;
 wherein the liposome is coupled to the peptide fatty acid conjugate through the fatty acid; and
 wherein the liposome lyses at a pH from 6.5 to less than 7.4, and the composition is non-cytolytic at physiological pH.

3. The composition of claim 2, wherein a diagnostic agent is encapsulated in the liposome.

4. The composition of claim 3, wherein the diagnostic agent is detectable by a detector selected from the group consisting of optical, electrical, electrochemical, magnetic, electromagnetic and acoustic detectors.

5. The composition of claim 2, wherein a therapeutic agent is encapsulated in the liposome.

6. A method of making the composition of claim 2, comprising:
 reacting a peptide fatty acid conjugate selected from the group consisting of SEQ ID NOS: 1, 2 and 6 with a liposome having a therapeutic or diagnostic agent encapsulated therein; and
 wherein the fatty acid binds to the liposome and forms the composition.

7. A method of delivering a therapeutic or diagnostic agent, comprising administering the composition of claim 2.

* * * * *

UNITED STATES PATENT AND TRADEMARK OFFICE
CERTIFICATE OF CORRECTION

PATENT NO. : 7,718,613 B2
APPLICATION NO. : 10/250641
DATED : May 18, 2010
INVENTOR(S) : Harmesh Singh Aojula and David John Clark It is certified that error appears in the above-identified patent and that said Letters Patent is hereby corrected as shown below:

Column 9, line 7 of Table I: Delete "(TLLEFLLEELLEFL)" and replace with -- (TLLEFLLEELLEEL) --.

Column 9, line 10 of Table I: Delete "Myr-WB" and replace with -- Myr-WE --.

Column 9, line 11 of Table I: Delete "Myr-GIGAY" and replace with -- Myr-GIGAV --.

Column 10, line 40: After "incubated for" delete "filter" and replace with -- further --.

Column 11, line 59: Delete "2001" and replace with -- 200 --.

Column 13, line 27: After "buffer to" delete "41" and replace with -- 4 --.

Column 13, line 28: Delete "Hposomes" and replace with -- liposomes --.

Signed and Sealed this

Nineteenth Day of October, 2010

David J. Kappos
*Director of the United States Patent and Trademark Office*